(12) United States Patent
Bullard

(10) Patent No.: US 9,107,704 B2
(45) Date of Patent: Aug. 18, 2015

(54) ANTERIOR CERVICAL INSTRUMENTATION SYSTEMS, METHODS AND DEVICES

(71) Applicant: Bullard Spine, LLC, Raleigh, NC (US)

(72) Inventor: Dennis E. Bullard, Raleigh, NC (US)

(73) Assignee: BULLARD SPINE, LLC, Raleigh, NC (US)

( * ) Notice: Subject to any disclaimer, the term of this patent is extended or adjusted under 35 U.S.C. 154(b) by 0 days.

(21) Appl. No.: 14/561,607

(22) Filed: Dec. 5, 2014

(65) Prior Publication Data

US 2015/0088206 A1    Mar. 26, 2015

Related U.S. Application Data

(63) Continuation of application No. 14/291,211, filed on May 30, 2014, now Pat. No. 8,920,478, which is a continuation of application No. 14/016,362, filed on Sep. 3, 2013, now Pat. No. 8,740,951, which is a (Continued)

(51) Int. Cl.
| | |
|---|---|
| *A61B 17/88* | (2006.01) |
| *A61B 17/70* | (2006.01) |
| *A61B 17/80* | (2006.01) |
| A61B 17/56 | (2006.01) |
| A61B 17/68 | (2006.01) |

(52) U.S. Cl.
CPC ......... *A61B 17/7059* (2013.01); *A61B 17/8014* (2013.01); *A61B 17/8023* (2013.01); *A61B 17/88* (2013.01); A61B 2017/564 (2013.01); A61B 2017/681 (2013.01)

(58) Field of Classification Search
None
See application file for complete search history.

(56) References Cited

U.S. PATENT DOCUMENTS

| 7,527,641 | B2 | 5/2009 | Suh |
| 8,147,529 | B2 | 4/2012 | Bullard |
| 2006/0217721 | A1 | 9/2006 | Suh |
| 2008/0234681 | A1 | 9/2008 | Baynham |

(Continued)

OTHER PUBLICATIONS

Jong-Pil, "Biomechanical Evaluation of the Pullout Strength of the Dynamic Osteosynthesis Construct (DOC) Anterior Cervical Planting System: A Comparison Between the Screw Angulations to Consider the Concept of Tiangulation," Journal of Korean Neurosurgery Society, v. 36, Jul. 2004; pp. 52-58.

(Continued)

*Primary Examiner* — Sameh Boles
(74) *Attorney, Agent, or Firm* — Troutman Sanders LLP; James E. Schutz; Parker D. Hancock

(57) ABSTRACT

Anterior cervical instrumentation systems, methods, and devices are disclosed. Systems may facilitate immobilizing or providing support for the cervical portion of the vertebral column of a patient. A device may comprise a plate having two channels located in a proximal to distal direction, and may further comprise at least one aperture. The device may further comprise attachment elements such as attachment cross-links and spacer cross-links, and fasteners. The plate and the attachment elements may be secured to the vertebrae by passing fasteners through apertures and channels. The length of the plate, position and number of the attachment cross-links, position and number of spacer cross-links and degree of movement may be intraoperatively selected by the surgeon to provide an optimal application and procedural outcome. Uniform components of the devices and systems allow for a more streamlined and simplified method of treating spinal conditions.

13 Claims, 18 Drawing Sheets

Related U.S. Application Data continuation-in-part of application No. 13/405,926, filed on Feb. 27, 2012, now Pat. No. 8,523,917, which is a continuation of application No. 12/554,220, filed on Sep. 4, 2009, now Pat. No. 8,147,529.

(60) Provisional application No. 61/094,340, filed on Sep. 4, 2008.

(56) References Cited

U.S. PATENT DOCUMENTS

| | | | |
|---|---|---|---|
| 2008/0249569 A1 | 10/2008 | Waugh et al. | |
| 2009/0043341 A1* | 2/2009 | Tyber et al. | 606/283 |
| 2010/0114176 A1 | 5/2010 | Ibrahim et al. | |
| 2010/0286781 A1 | 11/2010 | Bullard | |

OTHER PUBLICATIONS

Bachus et al., "Dynamic Cervical Plates: Does Load Sharing Cause Instability?" 46th Annual meeting Orthopaedic Research Society; Mar. 12-15, 2000; p. 355.

Sonntag, "Discovery of the Spine Specialist: Instrumentation of Cervical Spine," Barrow Neurological Institute, Phoeniz, AZ; 2008 PowerPoint presentation; pp. 1-16.

Jin et al., "Cortical Margining Capabilities of Fins Associated with Ventral Cervical Spine Instrumentation," Yonsei Medical Journal, vol. 46, No. 3, 2005; pp. 373-378.

One page PowerPoint picture from http://www.medscape.com; 2008.

* cited by examiner

ANTERIOR CERVICAL INSTRUMENTATION SYSTEMS, METHODS AND DEVICES

This Application is a continuation application claiming priority under 35 U.S.C. §120 to U.S. patent application Ser. No. 14/291,211, filed 30 May 2014, which is a continuation of U.S. patent application Ser. No. 14/016,362, filed 3 Sep. 2013, which issued as U.S. Pat. No. 8,740,951, which is a continuation-in-part application of U.S. patent application Ser. No. 13/405,926, filed 27 Feb. 2012, which issued as U.S. Pat. No. 8,523,917, which is a continuation of U.S. patent application Ser. No. 12/554,220, filed 4 Sep. 2009, which issued as U.S. Pat. No. 8,147,529, which claims priority under 35 U.S.C. §119(e) to U.S. Provisional Patent Application No. 61/094,340 filed 4 Sep. 2008, all of which are hereby incorporated in their entireties as if fully set forth herein.

TECHNICAL FIELD

Embodiments of the present invention relate to implantable surgical stabilization systems, devices, and methods for use in spinal surgery, and particularly to systems, methods, and devices that stabilize the cervical spine or other osseous structures.

BACKGROUND

Fusion of spinal vertebrae is often necessary to relieve debilitating pain or to correct a deformity. Cervical spinal fusion is often prescribed for patients suffering from degenerative disk disease whose symptoms may include neck pain of discogenic origin with degeneration of the disk confirmed by patient history and radiographic studies, trauma including fractures, tumors, deformity such as kyphosis, lordosis or scoliosis, pseudoarthrosis, or failed previous fusions.

Spinal surgical fusion is the process of bringing together two or more vertebrae under conditions whereby the vertebrae fuse together to form a unitary member of the spinal column. When vertebrae are fused, e.g., with bone grafts, graft extenders, or interbody spacers such as interbody cages or boxes (collectively termed "grafts" herein), it is desirable to stabilize the fused vertebrae using an apparatus such as a plate to fixate one cervical vertebra to another to promote fusion across motion segments. In carrying out the procedure, the members must be brought together under conditions that are critically controlled to prevent infection, maintain alignment of opposing members, and allow for the stress in the bone that is generated as the healing process matures. Immobilization is an important requirement during this healing process.

Another common spinal ailment is the degeneration of an intervertebral disc caused by trauma, disease, and/or aging. A degenerated intervertebral disc may have to be partially or fully removed from a spinal column. Partial or full removal of an intervertebral disc may destabilize a spinal column. Destabilization of a spinal column may alter the natural separation distance between adjacent vertebrae. Maintaining a natural separation distance between vertebrae may help prevent pressure from being applied to nerves that pass between vertebral bodies. Excessive pressure applied to the nerves may cause pain and/or nerve damage. During a spinal fixation procedure, a spinal implant may be inserted in a space created by removal or partial removal of an intervertebral disc between adjacent vertebrae. A spinal implant may maintain the height of the spine and restore stability to the spine. Intervertebral bone growth may fuse the implant to adjacent vertebrae.

A spinal implant may be inserted during a spinal fixation procedure using an anterior, lateral, or posterior spinal approach. A discectomy may be performed to remove or partially remove a defective and/or damaged intervertebral disc. A discectomy creates a disc space for a spinal implant. After a discectomy, a spinal implant may be inserted into the disc space. One or more spinal implants may be inserted between a pair of vertebrae. Spinal implants may be inserted into disc spaces prepared between more than one pair of vertebrae during a spinal fusion procedure.

A spinal plate may be coupled to vertebrae after insertion of one or more spinal implants. A spinal plate may stabilize the vertebrae and inhibit back out of the spinal implant from between vertebrae. A spinal plate may share a compressive load applied to one or, more spinal implants inserted between vertebrae. Fasteners, such as bone screws, may couple the spinal plate to vertebrae. Spinal plates may stabilize sections of cervical spine and/or sections of lumbar, spine.

The process of bone healing has been widely studied. Micro fractures, once thought to be negative events, are now seen as part of the natural process of bone remodeling and occur within bone in the course of everyday wear and tear. In the early stage of these cycles, bone resorption is first accomplished by osteoclasts. This is followed by new bone formation by osteoblasts over the latter part of each cycle. Osteoblasts serve a critical role in new bone formation, filling in the bony cavity in areas of bone remodeling with bone matrix. Osteoblasts are further known to release cytokines to attract osteoclasts. Osteoclasts serve to release proteases, which act to dissolve bone mineral matrix, collagen, and clear away damaged bone. Osetoclasts also releases matrix-bound growth factors and may serve as a chemo attractant for osteoblasts. The process of bone healing is currently believed to be a continual cycle, in which the body's response to microfractures and stress injuries within healing bone actually serve to strengthen healing ultimately and produce more solid bone.

What is needed are systems, methods and devices such as a plating system to repair bone fractures or to stabilize separate bony structures and allow them to fuse into a single item that may incorporate or harness the elements of the natural bone healing process. What are needed are systems, methods and devices that promote optimal fusion at a graft, particularly at cervical vertebrae. Further, methods, systems and devices that utilize a minimum number of parts and which may be easily customized intraoperatively by the surgeon are also needed.

SUMMARY

The present invention is directed to spinal instrumentation systems, methods and devices. The present invention comprises plating systems for use in spinal treatments, including, but not limited to, the cervical spine. Embodiments of the present invention are directed to anterior cervical instrumentation systems. Such systems may facilitate immobilizing or providing support for the cervical portion of the vertebral column of a patient. Such systems are composed of plates and screws for aligning and holding vertebrae in a desired position relative to one another. The systems may be "stand alone" as instrumentation is applied only to the anterior portion of the vertebral column (cervical vertebrae), or the systems may include other devices or compositions such as instrumentation on the posterior vertebral column. The systems, methods and devices allow a surgeon to modify and customize system components intraoperatively for optimal fit.

The present invention comprises systems, methods and devices comprising an implantable device for affixing to the anterior side of vertebrae, such as cervical vertebrae, for stabilizing the spinal column. Systems and devices of the present invention comprise a plate having an anterior surface and a posterior surface. A plate may comprise two parallel elongate channels extending from the distal end of the plate to the proximal end of the plate. Each of the channels forms an elongated opening through plate. A plate may further comprise at least one aperture, which may be centrally located, or at least one aperture at both the distal and proximal ends, and for stability reasons, may comprise two apertures at both the distal and proximal ends. The apertures may function in attaching the plate to a spinal vertebra using fasteners, such as screws. For example, apertures may be round, oval or rounded rectangular or combinations of these or others in shape. The systems may comprise a plurality of different length plates, which allows a surgeon the flexibility to select the desired length plate pre- or intraoperatively.

Systems and devices of the present invention may further comprise attachment elements for attaching the plate to one or more spinal vertebrae or for stabilizing the plate device. For example, a system and device may comprise a plurality of elements referred to herein as cross-linking elements. Cross-linking elements comprise at least two types of elements which may be similar in design, but differ in function. The two types of cross-linking elements comprise attachment cross-links and spacer cross-links and, for example, each may be a small bar that is as long as the plate is wide, with a defined width, that has two apertures, and each aperture may have the diameter of the apertures of the plate, and may also be sized so that a fastener, such as a screw, is sized to pass through the cross-linking aperture and also pass through the channel. Cross-linking element apertures may be located near both ends of a cross-linking element so that the apertures of the cross-linking elements align with each of the two channel openings in a plate.

The attachment elements comprise fasteners, elements for directly attaching the plate or attachment cross-links to the vertebrae, or attaching spacer cross-links to the plate, and such fasteners may comprise pins, dual head pins or screws. Fasteners may be sized to pass through the apertures of the cross-linking elements, the channels, and the apertures of the plates. Fasteners comprise a pin having two heads, wherein each head is spaced apart so that each pin head may enter a plate channel or two adjacent apertures.

Methods of the present invention comprise methods of spinal treatment, including treatment of the cervical spine. Methods comprise approaching the cervical spine from an anterior position. Using a template of a plate of the present invention, the exact location and placement of a plating system and device on the patient is determined. The template may be used on the exposed vertebrae or on x-rays or other visualizations of the spinal area. The size of plate to be used, the number cross-linking elements and attachment sites, where the attachment elements are to be placed through the plate apertures and the cross-link apertures is determined. Thus, the size of the plate and cross-link placement may individualized for the patient during the surgical procedure.

The appropriately sized plate may then be placed over the anterior portion of the vertebrae and anchored in place by the placement of fasteners, such as screws, through the at least one aperture, such as those found on the proximal and distal ends of the plate. The plate may be held in place with a temporary fastener, including but not limited to, a dual-headed pin. The pin is temporary in that the pin is placed through the plate to temporarily anchor the plate to the bone(s), for example to examine placement of the plate and alignment of the pin, and then the pin is removed. The pin may serve as a guide for bone screws which anchor the plate in place.

The proximal and distal apertures of a plate can be of several types. The first type may have the apertures of the same size and be round in shape, which allows for semi-constrained movement at the screw heads. Another type may have proximal and distal apertures that would be slightly elongated in the vertical axis, referred to herein as oval, to allow for translational movement at the proximal and distal ends of the plate. Another type may have proximal and distal apertures that would be elongated in the vertical axis, referred to herein as rounded rectangular, to allow for translational movement at the proximal and distal ends of the plate.

One or more attachment cross-links may be placed on the anterior side of the plate in the predetermined locations for attachment of the plate to the vertebrae, and attached to the vertebrae. For example, the plate and attachment cross-link may be attached to a spinal vertebra by passing a screw through each of the apertures of the cross-link and the parallel channels of the plate, and into the bone. The attachment cross-link may be fixed in position relative to the bone, but may move relative to the plate as the screws move in the parallel channels of the plate. Alternatively, the attachment cross-links may be spring loaded to lock it in position relative to the plate. The attachment cross-link may be positioned relative to the plate at any point along the length of the channels. Consequently, the surgeon may custom fit the location of the attachment cross-link to the bone because the position is not limited by predetermined screw holes in the plate.

Once one or more attachment cross-links are coupled to the vertebral bones, spacer cross-links may be fastened to the plate. The spacer cross-links do not attach to vertebrae, but fill the channel space on the device where the attachment cross-links are not present and function to stabilize the device. The entire length of the channels of the plate that are not occupied by the attachment cross-links may be filled with the spacer cross-links until there remains little or no open space in the channels of the plate. The spacer cross-links may be attached to the plate using a variety of fasteners, including, but not limited to, a hole-to-hole clamp or a screw head, or a short screw. The distance between the cross-links may be determined by the surgeon to create a range of travel of the attachment cross-link to provide a desired degree of subsidence. In this manner, the attachment cross-link attached to the bone may be locked in place relative to the plate or may have a predetermined degree of movement. The fasteners for attaching the plate device to the bone, such as screws, may be maintained in place by using locking heads or other designs known in the art.

An aspect of the present invention comprises systems, methods and devices wherein the plates may be provided in multiple lengths, but the apertures of the plates and the cross-linking elements, and the channel sized openings are uniform and allow for the use of the same size and style fastener head, such as the same screw head, for attachment of cross-linking elements, though the lengths of the fasteners may be a variety of lengths. This allows the surgeon to use one instrument, such as the same screw driver implement, to attach the plate to the vertebrae and to stabilize the device. The size, such as length and width of the cross-linking elements, is uniform and may be used with any length plate. This uniformity allows for a more simplified system for the surgeon to use, and for fewer tools to be needed in the operating theater.

An exemplary embodiment of the invention can be a vertebral stabilization device that can comprise an elongate plate. The plate can have a distal end and a proximal end and can comprise a first elongate channel and a second elongate channel. The first and second elongate channels can be substantially parallel and extend along at least a portion of the plate between the distal end and the proximal end, wherein each of the first and second elongate channels can have an interior surface. At least a portion of the interior surfaces can comprise a plurality of channel grooves. The plate can further comprise a first attachment cross-link, the first attachment cross-link can have a first aperture and a second aperture, and the first and second apertures can be configured to be aligned with the first and second elongate channels. In an embodiment, at least a portion of at least one outer surface of the first attachment cross-link can comprise a plurality of cross-link grooves adapted to cooperatively engage the plurality of channel grooves of the interior surface of at least one of the first and second elongate channels.

These and other features as well as advantages, which characterize various aspects of the present invention, will be apparent from a reading of the following detailed description and a review of the drawings.

DETAILED DESCRIPTION

Figure 1A:
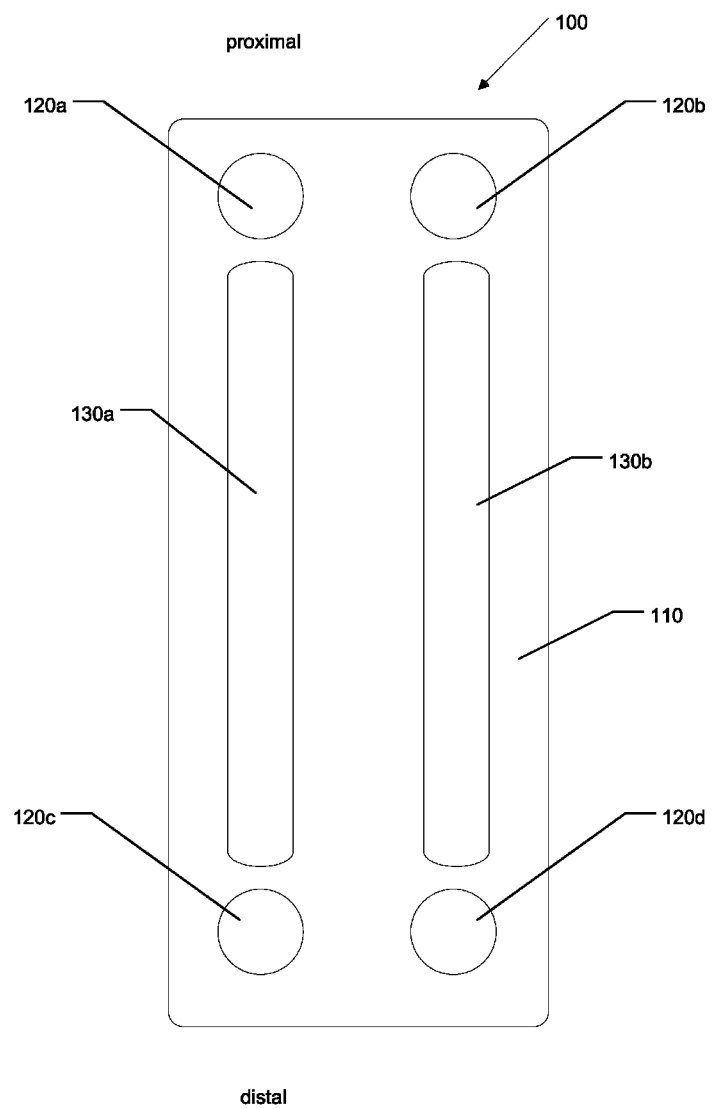
FIG. 1A illustrates an exemplary embodiment of a plate of the present invention.

The present invention comprises methods, systems and devices for treatment of spinal vertebrae, such as cervical vertebrae. The present invention comprises implantable devices comprising plates and attachment elements that allow for aligning and maintaining adjacent vertebrae, including but not limited to, cervical vertebrae, in a selected spatial relationship. The present invention may be used in spinal fusion methods.

The present invention comprises anterior cervical plating systems and devices that allow for the intersegmental compression of the spinal segment, such as compression of the adjacent vertebrae and the fusion graft in the disc space between the adjacent vertebrae, in lordosis, and where desired, multisegmental compression. For example, a device of the present invention comprises a plate, attachment elements comprising cross-linking elements comprising attachment cross-links and spacer cross-links, and fasteners, elements for directly attaching the plate and cross-linking elements to the bone, or attaching cross-linking elements to the plate, including, but not limited to, screws and dual-headed pins. For example, a system of the present invention comprises a plurality of plates of various lengths, and uniformly sized attachment elements and fasteners with uniform head design, and having multiple lengths. The invention further comprises tools and instruments used with such systems and devices in methods of spinal treatment such as drills, taps, screw drivers and the like.

Systems and devices of the present invention comprise a plate, which may be provided in a length that is sufficient to span a disc space and to overlap, at least in part, at least two adjacent cervical vertebrae. The anterior and posterior surfaces of a plate may be the same or may be different, in that one of the surfaces, such as the posterior surface which faces the vertebrae, may be textured and/or treated to induce bone growth or aid in attachment or stability. The plate, and other elements of the systems and devices, may be made of the same or different materials, such as steel, titanium, plastics, ceramics, or other biocompatible materials that have the structural strength and durability to withstand the cyclical loading associated with long term fixation. Materials that are also compatible with visualization systems, such as fluoroscopy or MRI, are also contemplated by the present invention. The plate and other elements may also comprise bioresorbable materials, bone in-growth materials, and/or growth promoting materials. For example, such bioresorbable, bone in-growth, or bone growth promoting materials may be found on surfaces of the plate and/or attachment elements such as screws. A plate of the present invention may be curved transverse to the longitudinal axis to conform to the anterior surface of a vertebrae, or may be curved along the longitudinal axis to conform to the lordotic curvature between the vertebrae, or may not be curved at all, or may be made of a material so that a surgeon or other personnel may curve the plate at the time of surgery, or may be made of a material that does not allow curving by a surgeon or other personnel.

A plate of the present invention comprises an anterior surface and a posterior surface and the two surfaces may be the same or different over the whole surface or a part of the surface areas. For example, the posterior surface, which directly faces the vertebrae surface, may be textured or coated with a material so as to encourage bone growth. For example, the anterior surface may be textured so as to allow better purchase of the attachment elements. The plate comprises a distal end and a proximal end. An aperture may be found on one or both of the distal or proximal ends, or may be located in a central position at the distal or proximal ends, or between the channels at one or both of the proximal or distal end areas, or in a midline position.

An example of a plate of the present invention comprises at least one aperture on both the proximal and the distal ends, and may further comprise at least two apertures on at least one of the proximal or distal ends, or at least two apertures on both the proximal and distal ends. The apertures may be the same size diameter or may have differently sized diameters. An example of the present invention comprises a plate having at least two apertures at both the proximal and distal ends that are of the same size diameter. An example of the present invention comprises a plate have at least one aperture at the midline of the plate equidistant between the channels. An example of the present invention comprises a plate having one or more apertures with the same size diameter or differently sized diameters. An example of the present invention comprises a plate having one or more apertures on the at least the proximal or distal end(s) where the apertures are longer in veritcal length than the screw head to allow for true translational movement at both ends.

Where the one or more apertures on the distal and proximal ends of the plate are round or where the aperture allows for little adjustment for screw placement, the movement of the plate is based upon semi-constrained movement at the screw heads. Where the one or more apertures on the distal and proximal ends of the plate are enlongated so that the vertical length is longer than the horizontal length, as in oval or rounded rectangular shaped apertures, there may be movement of the embedded screws in relation to the plate to allow for translational movement. Where the one or more apertures on the distal end are different from the one or more apertures on the proximal end, for example wherein rounded apertures are present on the proximal end to provide semi-constrained movement and one or more elongated or oval apertures are found at the distal end, translational movement is provided. Similarly, apertures in the cross-linking elements also allow for semi-constrained or translational movement depending on the shape of the aperture. The movement may be constrained by use of apertures having a particular shape that locks a screw tightly with the aperture. For example, the screw head and the aperture shape may be complementary so that a tight junction is formed between the screw head and the top of the aperture. For example, the aperture may be shaped like a star or other figure into which the screw head or a locking head fits exactly and constrains the movement at that location.

A plate of the present invention comprises at least two channels that are open from the anterior to the posterior surfaces, and which form openings that traverse a substantial portion of the length of the plate. The at least two channels run from an area near an aperture found at the distal end to an area near an aperture found at the proximal end, or where there are no apertures on the ends of the plate, the channels run from near the proximal end to near the distal end. The width of a channel may be the same or different size as the diameter of an aperture of a plate. An example of the present invention comprises a plate having two channels having widths of the channel openings that are the same as the diameter of the apertures of the plate, wherein the apertures of the plate have the same sized diameter.

Devices and systems of the present invention comprise attachment elements. Attachments elements comprise cross-linking elements and fasteners, elements that interact intimately with the bone or that attach cross-linking elements to a plate, such as screws and dual-headed pins. Cross-linking elements comprise attachment cross-links and spacer cross-links. Cross-linking elements are rectangular shaped bars that fit transversely across a plate, and for example, may be as long as a plate is wide. Cross-linking elements may have no apertures or at least one aperture. For example, a cross-linking element has two apertures that are located so that an aperture is on each end of the cross-linking element, so that when the cross-linking element is placed on the anterior surface of a plate, the cross-linking apertures align with the two channels of the plate. The apertures of a cross-linking element may have the same or different diameter as that of the plate aperture(s), and/or may have the same or different diameter as that of the width of the plate channels. An example of the present invention comprises a device having apertures of the same diameter, and having channel widths that are the same as the aperture diameters of the plate and the cross-linking elements. An example of the present invention comprises a device having apertures of the same diameter, and having channel widths that are the same as the aperture diameters or widths of the cross-linking elements.

An attachment cross-link is used for attaching the device to a bone, such as a vertebra. The attachment cross-link may have as many apertures as the plate has channels, for example, an attachment cross-link has two apertures that will align with two channels of a plate. An attachment cross-link is placed transversely across the anterior surface of a plate and an aperture of the attachment cross-link provides an opening though the cross-linking element and on through the channel opening of the plate. An attachment cross-link length may be shorter or longer than the width of the plate. An attachment cross-link may be as thick as or thinner than the thickness of the plate. An attachment cross-link may be textured on either its anterior or posterior surface, for example, so that texturing on its posterior surface meshes with texturing on the anterior surface of the plate, or either or both surfaces of the attachment cross-link may have a material that promotes bone in growth, bone growth, or aids in healing soft tissues. It is contemplated by the present invention that in use, an attachment cross-link is held with the device by the passing of a fastener such as a screw or pin through each of the aperture(s) of the attachment cross-link, through the channel opening of the plate and into the bone of the vertebrae. The head of the screw would engage with the attachment cross-link and the other end of the screw would be secured in the bone, and lock the attachment cross-link to the plate and the device to the bone.

A spacer cross-link is used for stabilizing the device. A spacer cross-link is placed transversely across the plate in the area of the channels where the attachment cross-link(s) is not present. In use, the spacer cross-links occupy the area between the proximal and distal ends of the plate where the channels are and provide stability to the device. A spacer cross-link may have as many apertures as the plate has channels, for example, a spacer cross-link has two apertures that will align with two channels of a plate. A spacer cross-link is placed transversely across the anterior surface of a plate and the two apertures of the spacer cross-link provide an opening though the cross-linking element and on through the channel opening of the plate. A spacer cross-link may be shorter or longer than the width of the plate. A spacer cross-link may be as thick as or thinner than the thickness of the plate. A spacer cross-link may be textured on either its anterior or posterior surface, for example, so that texturing on its posterior surface meshes with texturing on the anterior surface of the plate, or either or both surfaces of the spacer cross-link may have a material that promotes bone in growth, bone growth, or aids in healing soft tissues. It is contemplated by the present invention that in use, a spacer cross-link is held with the device by the passing of a fastener such as a short screw through each of the aperture(s) of the spacer cross-link, or by use of a spring loaded mechanism that clamps the spacer element to the plate, or by other methods of attachment. For example, the head of a short screw would engage with the anterior surface of the spacer cross-link and the other end of the screw may be flush with the posterior surface of the plate, which would lock the spacer cross-link to the plate.

A spacer cross-link may or may not be the same size, as in length, width, and/or thickness, as the attachment cross-link. For example, a system and device of the present invention comprise attachment cross-links and spacer cross links that are the same length, width and thickness, and have the same number and size apertures. Such a system and device would comprise only one type of cross-linking element that could be used for attachment and for spacing purposes. Such a system would use a fastener such as a screw, having only one diameter head, which may be provided in longer and shorter lengths, depending on the use of the cross-linking element, long for attachment and shorter for spacing. This would provide for use of only one type of screw driver. Such a system and device provides for uniform components to be used in implanting the device, and simplifies the methods and decisions performed by the surgeon.

Attachment elements of the present invention comprise fasteners, elements that interact intimately with the bone, or that attach cross-linking elements to a plate, such as bone screws, screws, bolts, pins, dual-headed pins, rivets, projecting elements, cements, plastics, or other components that may attach the plate to the bone or cross-linking elements to a plate. A description is provided herein comprising screws, but the invention is not necessarily limited to the use of only screws for this purpose. An aspect of the present invention provides for a device that allows for the placement of screws entering bone have sufficient angular freedom relative to the plate, in the variability of the axis of screw placement in the superior, inferior, medial and lateral directions. In the present invention, the surgeon may insert the bone screws into the vertebrae as to best to fit the anatomy of the individual patient, or multi-axial placement of a screw, such as at any angle up to 10-20 degrees from normal to the surface of the plate. The bone screws may be of a length that is sufficient for unicortical or bicortical placement. The bone screws may be self tapping, or may be inserted after tapping or drilling procedures, or after pin placement and removal. The bone screws may be locked into place with locking mechanisms known to those skilled in the art, such as a locking cap, locking ring, or a threaded cap. The screws used in the present invention for bone attachment may all be identical or different. For example, the screws used in the present invention are identical in length, width, and head design. For example, the screws used with attachment cross-links are identical to screws used with spacer cross-links in width and head design, but not in length.

Methods of the present invention comprise use of the systems and devices disclosed herein for treatment of spinal disease, damage or other conditions and pathologies. For example, a common approach for the surgical management of cervical disk disease is anterior cervical spinal fusion. The procedure for cervical spinal fusion is initiated by incising a small opening in the front of the neck. There is minimal trauma to the neck tissues. The damaged disk and/or bone spurs may be removed anterior to the spinal cord. This approach allows for minimal spinal or cord traction. Frequently, if there is significant spinal cord compression or if there is more than one disk level involved, a small plate is affixed on the anterior surface of the cervical vertebrae to provide greater permanent stability.

In a method of the present invention for anterior cervical spinal fusion, the following steps are performed. A template of a plate of the present invention may be used to determine placement of the plate, the attachment cross-links, the number of spacer cross-links needed, and the placement and angular location of the screws. A template is a replica of a plate of a particular length, and may be of a material that allows for visualization of the area under the template, i.e., may be transparent, and may be capable of having measurements written on it. The template may be used once the spinal vertebrae are exposed or may be used with x-rays or other visualization data. While the device components are being assembled based on the determinations made from the template placement, operating personnel may be preparing the vertebrae for insertion of screws, such as by pre drilling sites or tapping. Alternatively, no template is used and alternatively sized plates are used to make the determinations of placement and components.

A method of the present invention comprises temporary attachment of the plate to the vertebral bones. A plate may be held in place on the anterior spine temporarily by the use of pins, including, but not limited to, dual headed pins. The plate may be held in position using an instrument that allows for the insertion of temporary pins in apertures found at both the distal and proximal ends of a plate, or in the proximal and distal ends of elongated channels in plates that do not have end apertures. An inserter allows for a dual-head pin to be placed through the aperture or channel with visualization techniques, such as fluoroscopy. Use of the dual-headed pin and visualization allows the surgeon to determine the correct angle of placement for the screws that will follow the pins, to determine the correct length of the screws, and whether the plate is centrally and correctly aligned along the long axis of the vertebral bodies.

The dual-headed pins as disclosed herein are a single construct with an inserter that causes the pin heads to be placed in a parallel relationship. The placement of the pins under fluoroscopy aids in correct alignment in the sagittal and coronal planes. If the plate is correctly aligned coronally (not tilted to one side vertically), with lateral imaging, the dual pins will appear as one pin. If there is no or poor coronal alignment, two pins will show. If the pins are aligned coronally, but are not equally placed in the vertebral bodies, then under lateral visualization, the pins will be parallel, but one pin will appear to be deeper than the other pin.

The dual-headed pin, or any other pin known in the art, are contemplated to be of a sufficient size such that the placement in the bone and removal creates a tract or path for the bone screw or other fastener to follow. A pin or dual-headed pin may be disposable, in that it may be used only once, or may be reusable as long as the pin is structurally sound.

As an example, the surgeon can align the plate first and then select the best angle to place the pins under direct fluoroscopy. Pins, such as the dual-headed pin, may have pin heads of several lengths, ranging from about 8 to about 28 mm, from about 10 to about 25 mm, from about 12 to about 20 mm, from about 12 to about 16 mm, from about 15 to about 20 mm. Use of the pins allows for the estimation of the length of the bone screws to be used. The nonparallel angles of entry may prevent exact measurement of the length needed by the screws, but the present invention provides for a close approximation of the longest screws that can be safely used to attach the plate.

When elongated apertures are used, a dual-headed pin would be located in the upper portion of the upper (proximal) apertures, and the lower portion of the lower (distal) apertures, which would allow for translational dynamic movement once the device is assembled on vertebral bodies with screws or other attachment elements in place. For convenience, proximal and distal are in relation to the head, with items closer to the head being proximal.

To allow for true translational movement, the dual headed pin could have a 1-2 mm off-set on one side. This off-set would allow for pin placement in the upper end of the plate to have the off-set turned down and for pin placement in the lower end of the plate to have the off-set turned superior. The pins will fit into the upper portion of the upper (proximal) apertures and the lower portion of the lower (distal) apertures insuring the correct placement to allow translational dynamic movement. See FIG. 3C for a side view of a dual head pin with an offset, wherein the pin heads are offset from the central plane of the dual head pin. The b indicates the side of the pin with the offset, as does the ribbing on the handle 355, to indicate in which direction the pin heads are offset. See FIG. 3D for an example of placement of two dual headed pins with offset pin heads. In FIG. 3D, only one distal and proximal apertures are shown with pin placement and direction of the pin, indicated by a and b, are shown. The body of the pin is not shown. In practice, the dual headed pin with offset pin heads would be placed in the apertures, or in elongated channels, with the pins in the upper portion of the proximal apertures or channels and in the bottom of the lower (distal) apertures. The pin could be a single device that is flipped over for placement in either the upper or the lower apertures. The dual head pin could be labeled or color-coded to indicate the offset side. For example, FIG. 3C shows ribbing 355 on the side of the pin head offset for easy identification by a user.

In an embodiment where there are no end apertures and the at least two channels are elongated from the proximal area to the distal area, an aperture may be present in a central midline position between the channels. This central aperture may be used to provide minimal fixation of the plate without significant bone disruption during the initial placement of the plate for sizing. Once a pin is in place in the central aperture, differently sized plates could be placed on the pin to ascertain the correctly sized plate for that patient. Once the plate is selected, temporary dual-headed pins could be used to anchor the plate distally and proximally by putting in a pin at each end of the channels. The cross-linking elements and attachment elements such as bone screws can then be used to completely anchor the device to the vertebral bodies. The pins may be removed when the screws which replaced them are to be provided. Translational movement is possible with a plate having elongated channels without end apertures.

Once a compatible plate and attachment elements are determined, the plate may be attached to the selected vertebrae by providing temporary pin placements or by providing screws through the plate apertures to affix the plate at least at one end. The plate may be affixed to at least two vertebrae by providing screws through the distal and proximal end apertures, or by providing other attachment elements. The screws may follow a tract made by the placement and removal of a temporary pin, or one of the heads of a dual-headed pin. One or more attachment cross-links are added to the plate by providing temporary pins followed by screws or screws only or other fasteners only, through the attachment cross-link, through the channels of the plate and into the vertebral bone. Spacer cross-links are added to the plate, around the attachment cross-links, if necessary, or at least enough spacer cross-links are added to substantially cover the channels. The spacer cross-links may be attached by screws, spring loaded clamps, or other locking components. Once all of the determined attachment cross-links and spacer cross-links are added to the plate, the device is fully assembled and the surgical site may be closed.

Referring now in detail to the drawing figures, wherein like reference numerals represent like parts throughout the several views, FIG. 1A illustrates an exemplary embodiment of a plate 110 of an anterior cervical instrumentation system 100. The plate 110 may be substantially flat, as shown, or curved, not shown, and may have a thickness ranging from 1-3 millimeters (mm). In an embodiment, the plate 110 may be 2 mm thick. The plate 110 may be rectangular in shape, having a proximal and distal end. The plate 110 may measure 12-120 mms in length and 14-18 mms in width. In an embodiment, the plate 110 may be approximately 18 mms long and approximately 16 mms wide. The edges and corners of the plate 110 may be square, or rounded or smoothed to reduce potential damage or trauma to surrounding bone and/or tissue when implanted.

The plate 110 is adapted to be implantable in the human body, for example, on the cervical portion of the spine. The plate 110 may be composed of a suitable biocompatible or sterilizable material such as stainless steel, titanium, titanium alloys, memory alloys, nitinol, amorphous metal alloys, plastic, ceramic compounds, polymer compounds, carbon fiber, or another suitable material. The plate may be texturized, treated or coated on a portion or all of one or more sides to aid in joining of component parts, for bone growth or enhancement, to provide antimicrobial function, or immune response control.

The plate 110 may comprise a first aperture 120a and a second aperture 120b, both disposed at the proximal end of the plate 110. The radius of the apertures 120a and 120b may be between 4-6 mms. In an embodiment, the radius of the apertures 120a and 120b may be approximately 4.6 mms. The radius of the apertures 120a and 120b may correspond to the diameter of bone screws that will be used to secure plate 110 to the bone at a target site. The distance between the centers of the aperture 120a and 120b may be between 6-12 mms. In an embodiment, the distance between the centers of the aperture 120a and 120b may be approximately 9 mms. The plate 110 may further comprise a third aperture 120c and a fourth aperture 120d disposed at the distal end of the plate 110. The dimensions and arrangement of the third and fourth apertures 120c relative to the plate 110 may be substantially identical to the first and second apertures 120a and 120b.

The interior perimeters of the apertures 120a-d may be substantially cylindrical. In such embodiments, the apertures 120a-d are adapted to interface with a round head surgical screw or fastener. The head of such a fastener may extend above the surface of the plate 110 when threaded through one of the apertures 120a-d. This may not be optimal in situations where a minimal profile of the plate 110 and system 100 is desired. In other embodiments, at least a portion of the interior perimeter of the apertures 120a-d may be frusto-conical. In such embodiments, the apertures 120a-d may be adapted to interface and receive the angled surface of a flat head surgical screw or fastener. The head of such a fastener would be flush with the surface of the plate 110 when threaded though one of the apertures 120a-d.

In exemplary embodiments of the plate 110, the interior perimeter of the apertures 120a-d may be substantially smooth. The apertures 120a-d may be substantially wide enough to enable the entire width of the fastener, including the treads, to pass through. In such embodiments, the plate 110 would be secured to the surface of the bone at least partial due to the compression caused by tightening the screw or fastener. In other contemplated embodiments, the interior perimeter of the aperture 120a-d may be counter-threaded to correspond to the threading on a selected screw or fastener. In such embodiments, the fastener may be threaded through apertures 120a-d and engage the bone to provide a secure attachment of the plate 110 to the vertebrae.

The plate 110 may further comprise a first channel 130a and a second channel 130b. The first and second channels 130a and 130b span the thickness of the plate 110 to provide elongated openings in the plate. The first and second channels 130a and 130b are elongate and extend in the distal-proximal direction. The first channel 130a may be disposed between and axially aligned with the first and third apertures 120a and 120c. Similarly, the second channel 130b may be disposed between and axially aligned with the second and fourth apertures 120b and 120d.

The channels 130a and 130b may be adapted to receive a fastener substantially similar to the fasteners used to secure plate 110 to the vertebrae through apertures 120a-d as described above. The width of the channels 130a and 130b may be substantially equal to the width of apertures 120a-d. The length of the channels 130a and 130b may be between 14-100 mms. In an embodiment, the length of the channels 130a and 130b may be approximately 20 mms. The channels 130a and 130b may be centered between apertures 120a-d such that the ends of the channels 130a and 130b are equidistant from the nearest aperture 120a-d.

The interior perimeter of the channels 130a-130b may be substantially smooth. This may enable the body of a fastener passing through the channels 130a-130b to smoothly translate in the distal to proximal direction. This feature allows for the attachment cross-links elements, described below, to "float" relative to the plate 110.

The plate 110 may be adapted to attach to vertebrae using temporary pins, surgical screws or fasteners as described above as attachment elements. In particular, the plate 110 is adapted to be disposed on the anterior side of the cervical portion of the spinal column. In other contemplated embodiments, the plate 110 may by used in other regions of the spinal column or other bones of the body.

Figure 1B:
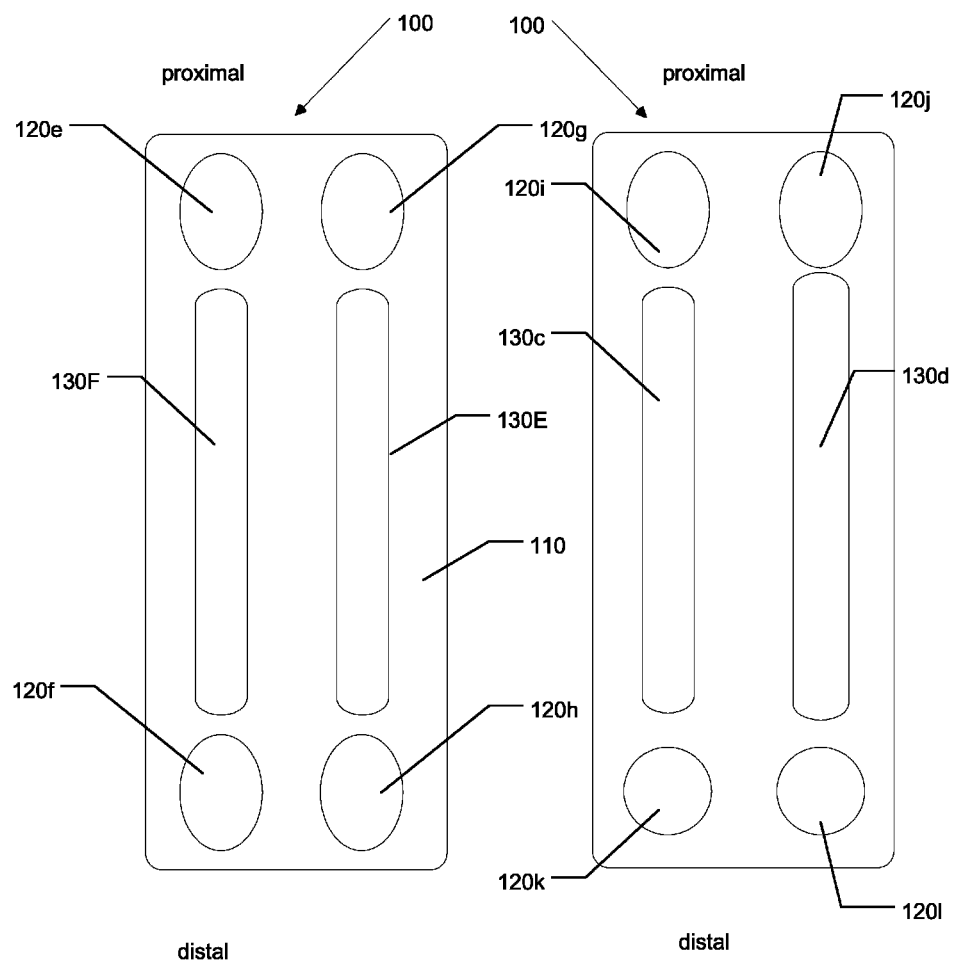
FIG. 1B illustrates an exemplary embodiment of a plate of the present invention.

FIG. 1B shows exemplary plates wherein the distal and proximal end apertures 120e-h are elongated, or wherein the proximal apertures 120i,j are elongated and the distal apertures 120k,l are round. For elongated apertures, the vertical length of the aperture may be 6-8 mm. The apertures and channels 130c,d may be as described in FIG. 1A.

Figure 1C:
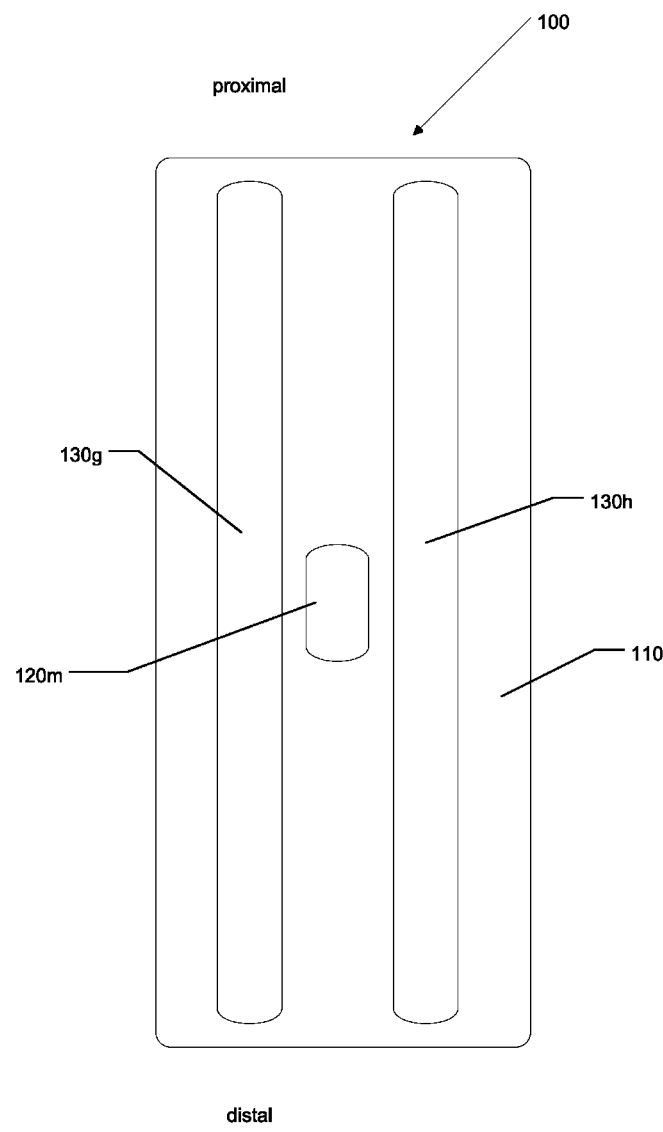
FIG. 1C illustrates an exemplary embodiment of a plate of the present invention.

FIG. 1C shows an exemplary plate wherein the channels 130g and 130h are located substantially from near the proximal end of the plate 110 to near the distal end of the plate 110, and provide an opening from the anterior to the posterior sides of the plate 110. There are no end apertures. A central midline aperture 120m is shown as an elongated aperture, but may be a round or other shaped aperture (not shown). The plate, aperture and channels may be as described for FIGS. 1A and 1B.

Figure 1D:
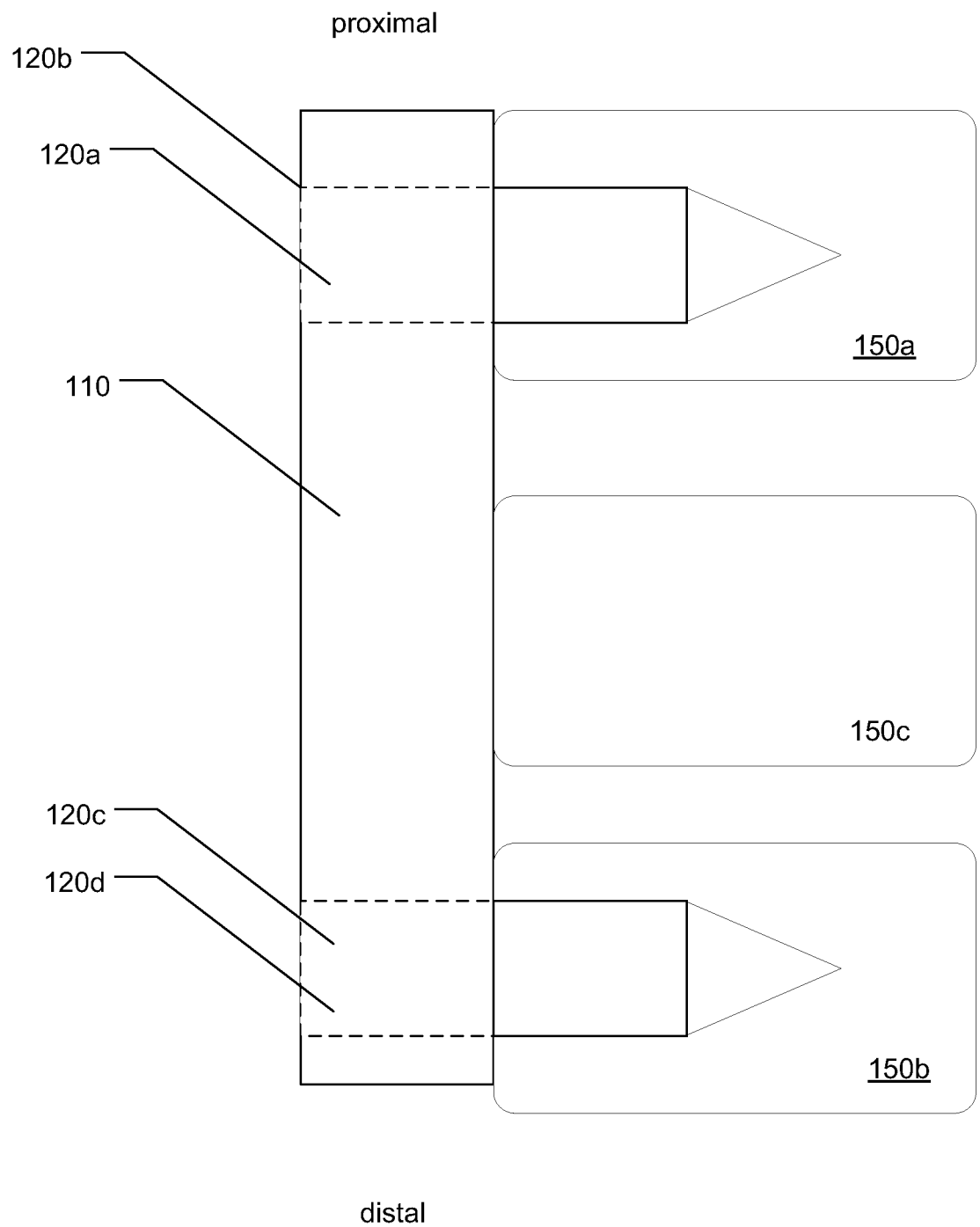
FIG. 1D illustrates a side view an exemplary embodiment of a plate attached to a region of the spinal column.

FIG. 1D illustrates a side view of an exemplary embodiment of a plate 110 attached to a region of the spinal column. The plate 110 may be attached to a first vertebra 150a by means of fasteners threaded through the first and second apertures 120a and 120b and engaging the bone. Because the depiction is a side view, it is difficult to distinguish in the illustration between the first and second apertures as one is directly behind the other. Further, the channels 130a and 130b are not depicted in the drawing.

The plate 110 may be positioned such that the proximal end is directly above the first vertebra 150a. The surgeon may maneuver the plate 110 such that the first and second apertures 120a and 120b are directly over a target drill site, or a site for placement of a dual-headed pin, or two pins. The surgeon may mark the drill sites, remove the plate 110, and use a guide to drill holes of the appropriate depth at the target drill sites. Alternatively, the surgeon may leave the plate in place and either use the plate as a drill guide or place a drill guide atop the plate to drill the necessary holes. Alternatively, the surgeon may leave the plate in place and provide a dual-headed pin through both apertures 120a and 120b simultaneously. A dual-headed pin or two pins may be placed through apertures 120c and 120d. One of the dual-headed pins is then removed, and the surgeon may then attach the plate 110 to the first vertebra using the selected screw or fastener. The other dual-headed pin or two pins are removed, and screws are placed through the plate apertures and into the bone.

The above process may be substantially repeated to attach the distal end of the plate 110 to a second vertebra 150b. This will lock the first and second vertebrae 150a and 150b in position relative to each other. The first and second vertebrae 150a and 150b are preferably on opposite sides of a target vertebra 150c or vertebrae undergoing treatment. The vertebra 150c undergoing treatment may be attached to the plate 110 using cross-linking elements, as will be described below.

Given the differences in anatomy and injuries between patients, and number of vertebrae undergoing treatment, the distance between suitable attachment sites on the first and second vertebrae may differ substantially from the distance between the first and second apertures 120a and 120b at the proximal end of the plate 110 and the third and fourth apertures 120c and 120d at the distal end. To enable optimal fitment, the system 100 may comprise a plurality of plates of variable lengths.

Figure 2:
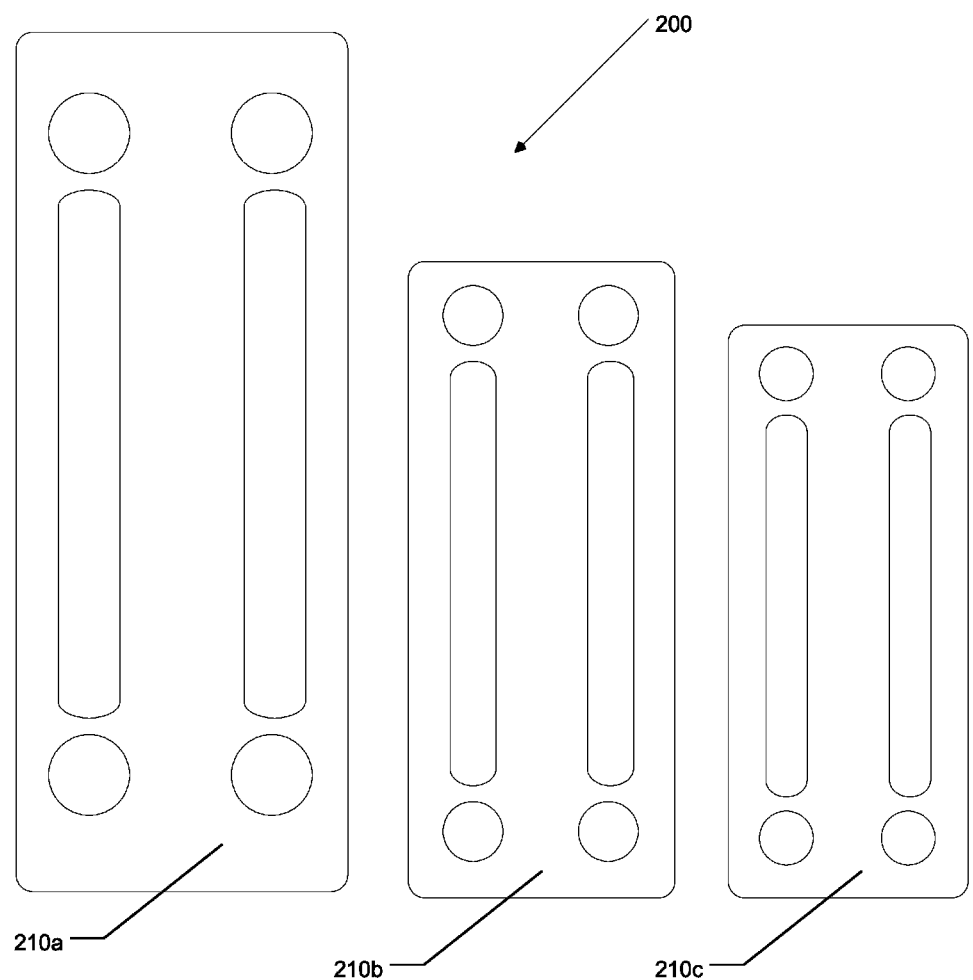
FIG. 2 illustrates an exemplary embodiment of a system having a plurality of plates.

FIG. 2 illustrates an exemplary embodiment of a system having a plurality of plates. In this exemplary embodiment, the system 200 may comprise a first plate 210a, a second plate 210b, and a third plate 210c. The plates 210a-c may be substantially identical in design and dimension to plate 110 with the exception of the overall length of the plates and the elongate channels. Alternatively, a system may comprise plates of differing lengths as shown in FIG. 2, but plates in each size may have differently shaped apertures, or a central aperture, and/or channels are exemplified in FIGS. 1A-C.

The plates 210a-c each may have a different length. In one embodiment, the difference between the lengths of the plates may be in an increment substantially equal to the height of a vertebra. In such an embodiment, the first plate 210a could be intended to attach to a first and second vertebra, as described above, which have three target vertebrae undergoing treatment located there between. The second plate 210b could be adapted to be used when two vertebrae are undergoing treatment. Similarly, the length of the third plate 210c could make it suitable for situations where a single vertebra is undergoing treatment.

In other embodiments, the difference in length between the plates 210a-c may correspond to the difference in lengths between desirable drilling sites on the vertebra of patients. For example, plates 210a-c could be similar in length and adapted for use in situations where a single vertebra is undergoing treatment. The differences in the length of plates 210a-c could correspond to the difference in the size of vertebra of patients. This would enable a surgeon to intraoperatively select the appropriate length plate to attach to the vertebra of a patient.

In other contemplated embodiments, the plates 210a-c could have a wide range of lengths accounting for both applications with one or more target vertebra and vertebra of different sizes. In such embodiments, the system 200 may comprise more plates that the three illustrated. For example, the plates may incrementally vary in length to span an operational range from the shortest to the longest plate that may feasibly be used.

Figure 3A:
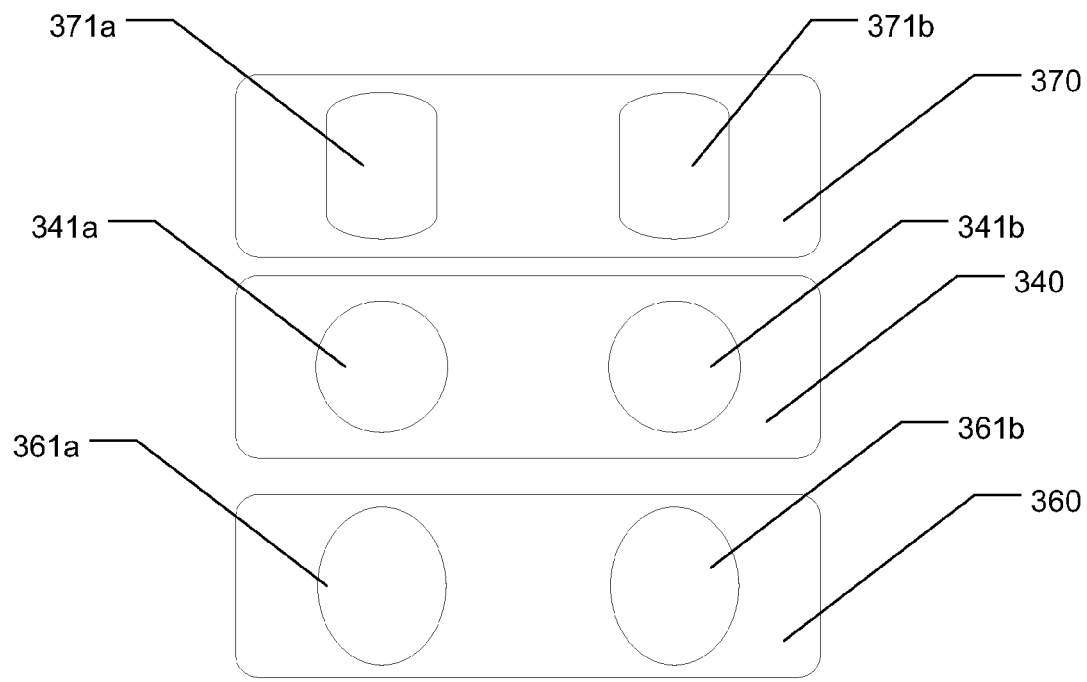
FIG. 3A illustrates three embodiments of cross-linking elements.

FIG. 3A illustrates embodiments of cross-linking elements. The cross-linking element 340 may be constructed from the same material as the plate 110 described above. The cross-linking element 340 may be substantially equal in length to the width of plate 110. The width of the cross-linking element 340 may be between 14-18 mms. In an embodiment, the cross-linking element may be 16 mm wide. The thickness of the cross-linking element 340 may be between 1-3 mms. In an embodiment, the cross-link may be 2 mm thick.

The cross-linking element 340 may comprise a first aperture 341a and a second aperture 341b. The dimensions and distance between apertures 341a and 341b may be substantially similar to those of apertures 120a and 120b.

The interior perimeters of the apertures 341a and 341b may be substantially cylindrical. In such embodiments, the apertures 341a and 341b are adapted to interface with a round head surgical screw or fastener. In other embodiments, a portion of the interior perimeter of the apertures 341a and 341b may be frusto-conical. In such embodiments, the apertures 341a and 341b may be adapted to interface and receive the angled surface of a flat head surgical screw or fastener.

In exemplary embodiments of cross-linking element 340, the interior perimeter of the apertures 341a and 341b may be substantially smooth. The apertures 120a-d may be substantially wide enough to enable the entire width of the fastener, including the threads, to pass through. In other contemplated embodiments, the interior perimeter of the aperture 341a and 341b may be counter-threaded to correspond to the treads on a selected screw or fastener.

The cross-linking element 360 may be constructed from the same material as the plate 110 described above. The cross-linking element 360 may be substantially equal in length to the width of plate 110. The width of the cross-linking element 360 may be between 14-18 mms. In an embodiment, the cross-linking element may be 16 mm wide. The thickness of the cross-linking element 360 may be between 1-3 mms. In an embodiment, the cross-linking element may be 2 mm thick.

The cross-linking element 360 may comprise a first aperture 361a and a second aperture 361b. The dimensions and distance between apertures 361a and 361b may be substantially similar to those of apertures 120a and 120b.

The cross-linking element 370 may be constructed from the same material as the plate 110 described above. The cross-linking element 370 may be substantially equal in length to the width of plate 110. The width of the cross-linking element 370 may be between 14-18 mms. In an embodiment, the cross-linking element may be 16 mm wide. The thickness of the cross-linking element 370 may be between 1-3 mms. In an embodiment, the cross-linking element may be 2 mm thick.

The cross-linking element 370 may comprise a first aperture 371a and a second aperture 371b. The dimensions and distance between apertures 371a and 371b may be substantially similar to those of apertures 120a and 120b.

Figure 3B:
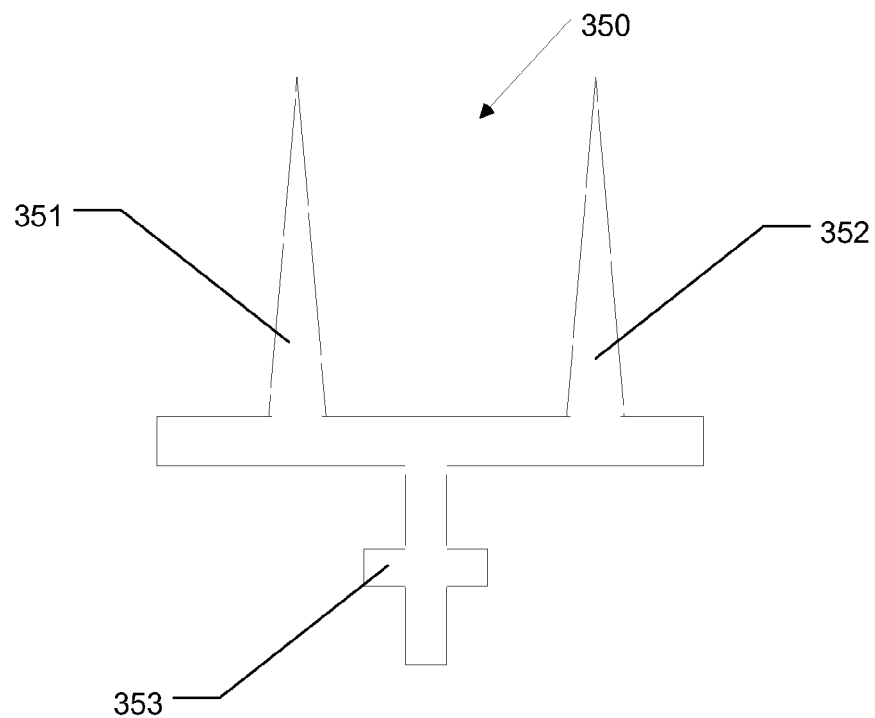
FIG. 3B illustrates an embodiment of a dual-headed pin.
Figures 3C, 3D:
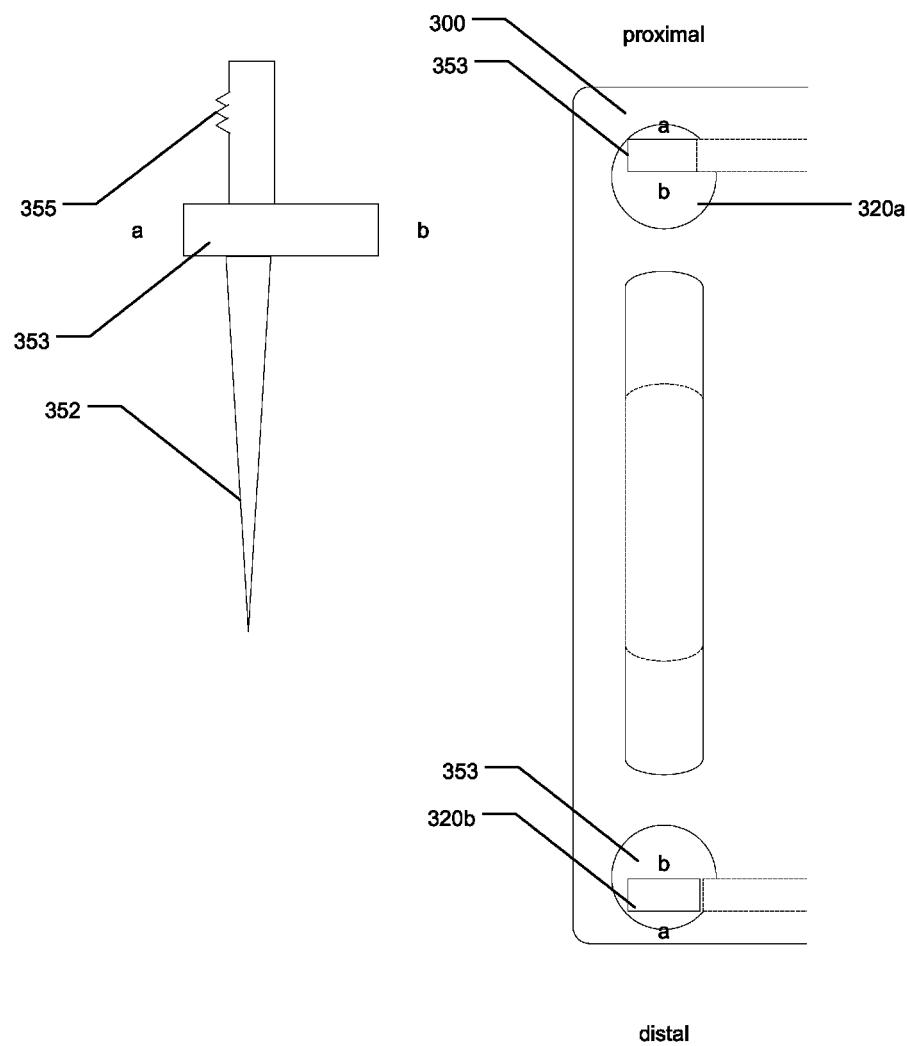
FIG. 3C illustrates an embodiment of an offset dual-headed pin.
FIG. 3D illustrates an embodiment of placement of an offset dual-headed pin.

FIG. 3B shows an exemplary dual-headed pin 350. The pin has two pin heads 351 and 352, and a handle 353. The pin heads may be from 12-20 mm and a system may comprise one or more dual-headed pins having at least one of each of the 12-20 mm lengths. The handle 353 may be of any length that is suitable for holding or tapping by the surgeon.

Figure 4A:
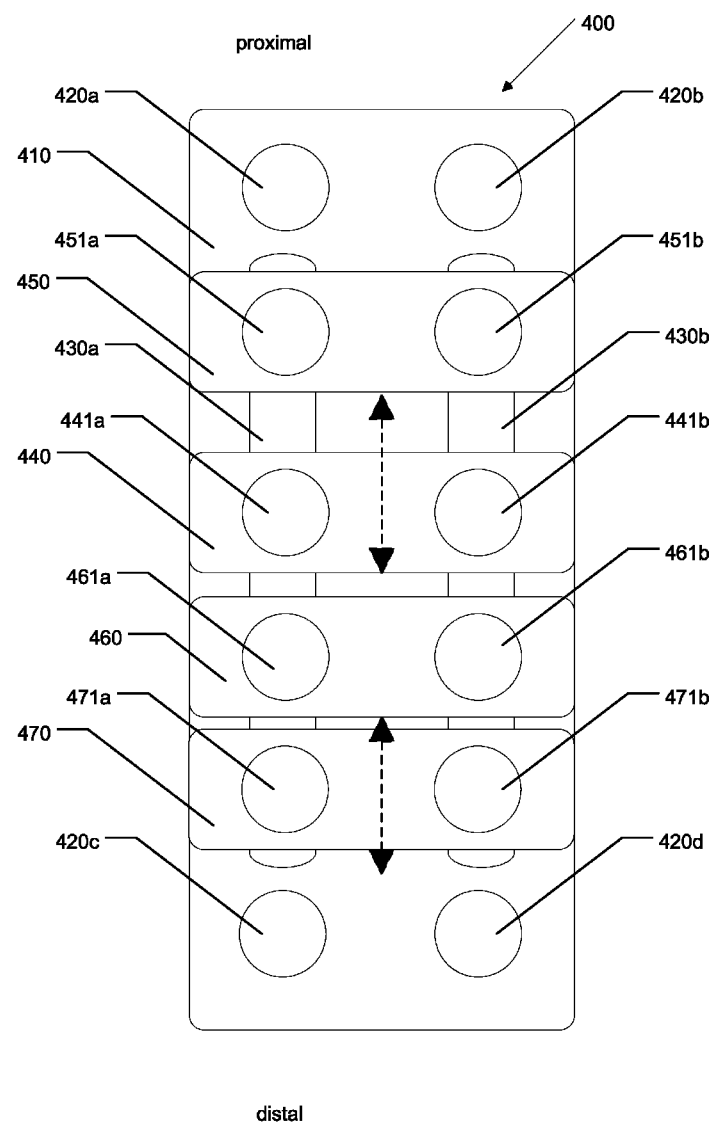
FIGS. 4A and B illustrate a top view of a plate and cross-linking elements of an exemplary embodiment of the present invention.

FIG. 4A illustrates a top view of a plate and cross-linking elements of an exemplary embodiment of the system. In an exemplary embodiment, the system 400 may comprise a plate 410 having apertures 420a-d, and cross-links. The plate 410 and cross-linking elements may be substantially similar to the plates and cross-linking elements described above. Cross-linking elements may be employed either as a spacer cross-link or as an attachment cross-link. In an embodiment, the system 400 comprises attachment cross-link 440 and 470, a first spacer cross-link 450, and a second spacer cross-link 460.

The attachment cross-link 440 may be coupled to the plate 410 by threading fasteners through apertures 441a and 441b and channels 430a and 430b, and engaging the vertebra disposed below the plate. In an embodiment, the attachment cross-link 440 is not fixed in position relative to plate 410. Rather, attachment cross-link 440 may move atop the plate 410 as the fasteners glide though channels 430a and 430b.

The attachment cross-link 470 may be coupled to the plate 410 by threading fasteners through apertures 471a and 471b and channels 430a and 430b, and engaging the vertebra disposed below the plate. In an embodiment, the attachment cross-link 470 is not fixed in position relative to plate 410. Rather, attachment cross-link 470 may move atop the plate 410 as the fasteners glide though channels 430a and 430b.

Spacer cross-links 450 and 460 may be disposed on both sides of the attachment cross-link 440 and proximal to cross-link 470 to limit their degrees of motion. In an exemplary embodiment, the first spacer cross-link 450 may be attached to the plate 410 on the proximal side of the attachment cross-link 440. The second spacer cross-link 460 may be attached on the distal side of the attachment cross-link 440, and proximal to attachment cross-link 470. The spacer cross-links 450 and 460 may be attached to the plate 410 using a fastener, such as a hole to hole clamp, a screw head, or short screw, by means of channels 430a and 430b and apertures 451a, 451b, 461a, and 461b. The spacer cross-links 450 and 460 may be fixed in position relative to the plate 410 upon attachment to the plate. In other contemplated embodiments, the spacer cross-links 450 and 460 may be spring loaded or employ spring loaded fastening elements to attach to the plate 410. There are multiple different spring loaded fastening elements known in the art and the decision for which fastening elements to use is within the knowledge of those skilled in the art.

The attachment position of spacer cross-links 450 and 460 may be selected to limit the range of motion of the attachment cross-links 440 and 470 as desired. The cross-links minimize rotational movement. Upon coupling to the plate 410, spacer cross-links 450 and 460 define how far attachment cross-links 440 and 470 may move along the plate 410 on channels 430a and 430b, as illustrated by the dashed arrows.

Figure 4B:
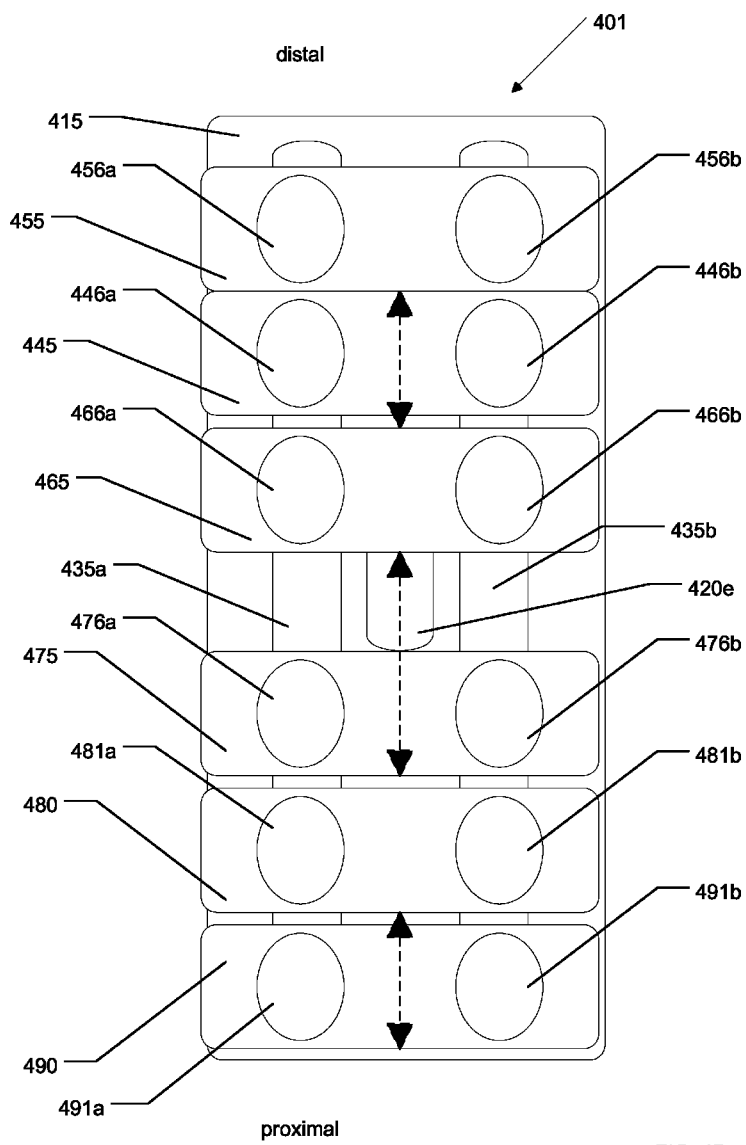

FIG. 4B illustrates a top view of a plate and cross-linking elements of an exemplary embodiment of the system. In an exemplary embodiment, the system 410 may comprise a plate 410 having only a central aperture 420e, two channels that are located from an area near the proximal end to an area near the distal end, and cross-linking elements. The plate 410 and cross-linking elements may be substantially similar to the plates and cross-linking elements described above. Cross-linking elements may be employed either as a spacer cross-link or as an attachment cross-link. In an embodiment, the system 410 comprises attachment cross-links 445, 475 and 490, and spacer cross-links 455, 465 and 480.

The attachment cross-links 445, 475 and 490 may be coupled to the plate 410 by threading fasteners through apertures 446a and 446b, 476a and 476b, 491a and 491b, respectively, and through channels 435a and 435b, and engaging the vertebrae disposed below the plate. In an embodiment, the attachment cross-links 445, 475 and 490 are not fixed in position relative to plate 410. Rather, attachment cross-link 445, 475 and 490 may move atop the plate 410 as the fasteners glide though channels 435a and 435b.

Spacer cross-links 455, 465 and 480 may be disposed on the plate 410 to limit the degrees of motion of attachment cross-links 445, 475 and 490. In an exemplary embodiment, spacer cross-link 455 may be attached to the plate 410 on the proximal side of the attachment cross-link 445. Spacer cross-link 465 may be attached on the distal side of the attachment cross-link 445, and proximal to attachment cross-link 475. Spacer cross-link 480 may be attached on the proximal side of the attachment cross-link 490. The spacer cross-links 455, 465 and 480 may be attached to the plate 410 using a fastener, such as a hole to hole clamp, a screw head, or short screw by means of channels 435a and 435b and apertures 456a, 456b, 466a, and 466b, 481a and 481b, respectively. The spacer cross-links 455, 465 and 480 may be fixed in position relative to the plate 410 upon attachment to the plate. In other contemplated embodiments, the spacer cross-links 455, 465 and 480 may be spring loaded or employ spring loaded fastening elements to attach to the plate 410. There are multiple different spring loaded fastening elements known in the art and the decision for which fastening elements to use is within the knowledge of those skilled in the art.

The attachment position of spacer cross-links 455, 465 and 480 may be selected to limit the range of motion of the attachment cross-links 445, 475 and 490 as desired. The cross-links minimize rotational movement. Upon coupling to the plate 410, spacer cross-links 455, 465 and 480 define how far attachment cross-links 445, 475 and 490 may move along the plate 410 on channels 430a and 430b, as illustrated by the dashed arrows. The attachment cross-links are also limited in movement by the ends of the channels 435a and 435b.

In other contemplated embodiments, multiple attachment cross-links could be used with a multiple spacer cross-links. For example, a spacer cross-link could be attached to the middle of the plate and attachment cross-links placed on either side. The ends of the channels 435a and 435b and the spacer cross-link would limit the range of motion of the attachment cross-links. In other embodiments, various configurations and spacer and attachment cross-links are contemplated to attain a desirable result for a particular application.

Figure 5:
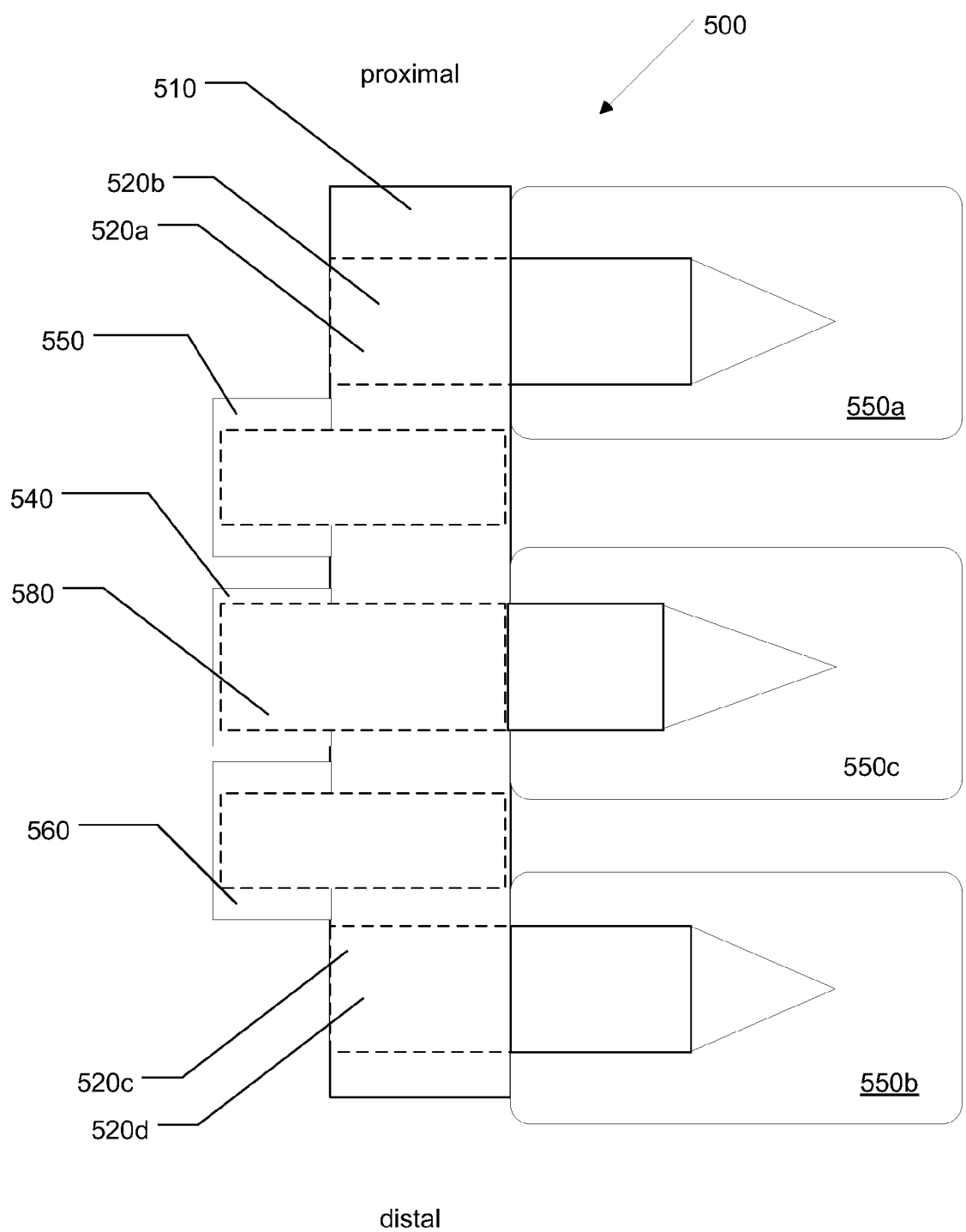
FIG. 5 illustrates a side view of an exemplary embodiment of the system attached to a spinal column.

FIG. 5 illustrates a side view of an exemplary embodiment of the device 500 and system attached to a spinal column. Plate 510 may be attached to a first vertebra 550a and a second vertebra 550b in substantially the same manner as plate 110 described above, using fasteners through apertures 520a-d. The attachment cross-link 540 may be placed atop plate 510 and attached to the a target vertebra 550c by passing a fastener 580 through the apertures of the cross-link 540 and channels (not pictured) of the plate 510 and engaging with a hole in the vertebra 550c.

Spacer cross-links 550 and 560 may be attached to the plate in a fixed position as described above. The attachment cross-link 540 may move along plate 510 as the fasteners glide through the channels of the plate 510. The movement of the attachment cross-link 540 is limited by the spacer cross-links 550 and 560. Attachment cross-link 540 may move upward until it comes in contact with the first spacer cross-link 550. Similarly, attachment cross-link 540 may move downward until it comes in contact with the second spacer cross-link 560.

Movement of attachment cross-link 540 enables the target vertebra 550c to move up and down, relative to the first and second vertebrae 550a and 550b. This movement or subsidence allows for bone-to-bone contact.

Figure 6A:
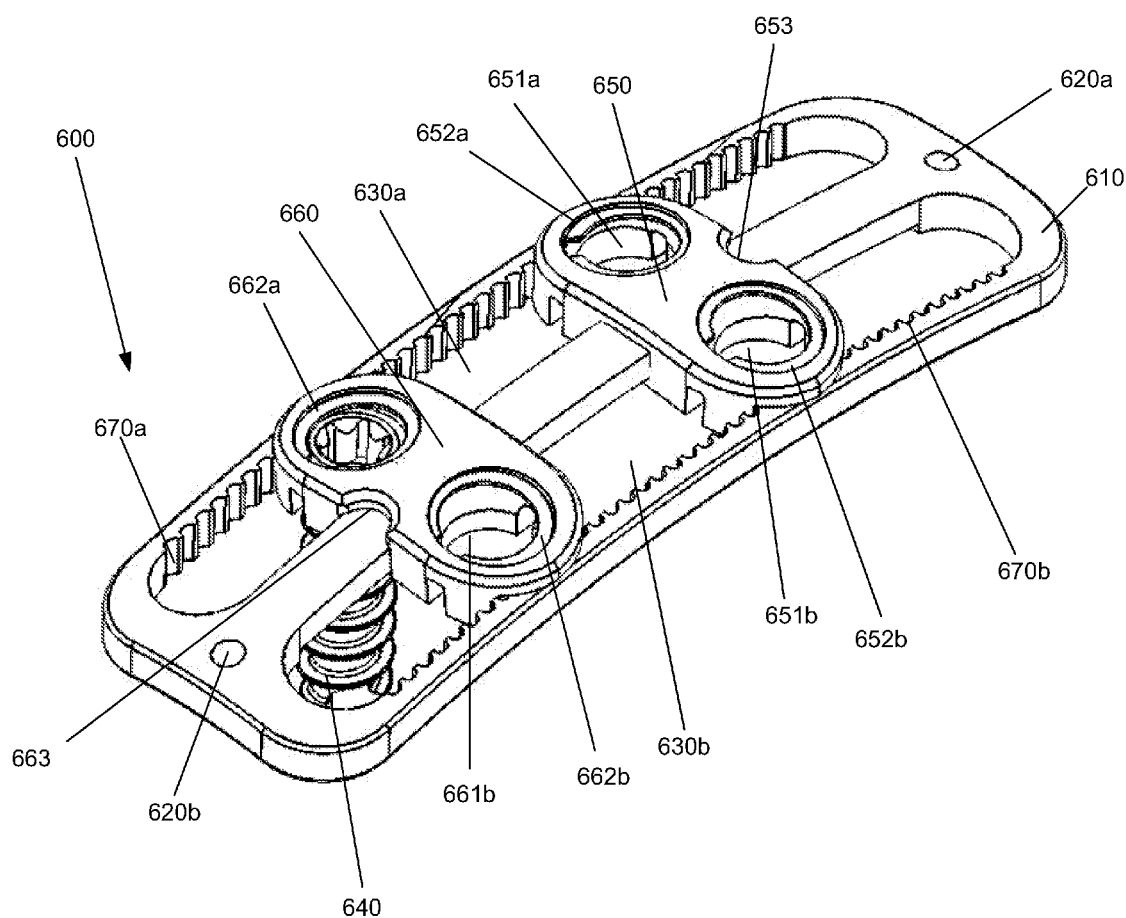
FIG. 6A illustrates a top view of a plate and attachment cross-links of an exemplary embodiment of the present invention.

FIG. 6A illustrates a top view of a vertebral stabilization device 600 that can comprise plate 610 and attachment cross-links 650 and 660 in an embodiment of the present invention. The elongate plate 610 can have a distal end and a proximal end and can have an anterior side and a posterior side and can be adapted to be implantable in the human body, for example, on the cervical portion of the spine. The elongate plate 610 can comprise a plurality of channels 630a-630b that can be configured to be coupled with attachment cross-link 650 and a fastener 640 such that the plate is coupled to two or more vertebra. Thus, the plate can stabilize the vertebra after surgery.

In one embodiment, the plate 610 can comprise a first elongate channel 630a and a second elongate channel 630b. The channels 630a and 630b can extend along at least a portion of the plate between the distal end and the proximal end. In one embodiment, the first elongate channel 630a and the second elongate channel 630b can be substantially parallel. In an embodiment, the first elongate channel 630a and the second elongate channel 630b can span the thickness of the plate 610 to provide openings in the plate 610. In embodiments where the elongate channels 630 span the thickness of the plate 610, attachment cross-links 650 and 660 can be placed at various points along the channels via coupling of the attachment cross-links 650 and 660 to the channels 630 through cross-link grooves and channel grooves 670a-670. This can provide a customizable, modular device that can be modified intra-operatively as the surgeon desires.

The channels 630a-630b can be adapted to receive a fastener 640 through an aperture 651a-b and 661a-b in the attachment cross-links 650 and 660 in order to secure the plate 610 to the vertebra. For example, the fastener can extend through an aperture in the cross-link and into a verterbra of a patient, thereby securing the device to the patient.

The channels 630a-630b can comprise an interior surface comprising a plurality of channel grooves 670a-670b disposed on at least a portion of the interior surface. In other embodiments, the channels 630a and 630b may include other attachment features to cross-link in a desired position along the plate 610. The interior surface can also be substantially smooth on at least a portion of the interior surface. In some embodiments, the channel grooves 670a can be disposed on the anterior side of elongate channel 630a and the channel grooves 670b can be disposed on the posterior side of the elongate channel 630b. The channel grooves 670a-670b can provide a means of engaging the attachment cross-links 650 and 660 to the plate 610, thereby securing the cross-links in a position along the plate 610.

The plate 610 can further comprise attachment cross-links 650 and 660 that can be configured to couple plate 610 to the vertebra. In one embodiment, the plate 610 can comprise a first attachment cross-link 650 and a second attachment cross-link 660. Several attachment cross-links can be used in order to provide multiple stabilization points. The attachment cross-links 650 and 660 can comprise a plurality of cross-link grooves on the outer surface of the cross-links. The cross-link grooves can be configured to cooperatively engage the channel grooves 670a-670b.

The attachment cross-links 650 and 660 can comprise a plurality of apertures 651a-651b and 661a-661b, respectively. In an embodiment, the attachment first attachment cross-link 650 can have a first aperture 651*a* and a second aperture 651*b*. In one embodiment, the second attachment cross-link 660 can comprise a third aperture 661*a* and a fourth aperture (not shown).

Apertures 651*a-b* and 661*a-b* can be configured to be aligned with the first and second elongate channels. Attachment cross-links 650 and 660 can be coupled to the plate 610 by one or more threaded fasteners 640 through apertures 651*a*-651*b* and 661*a*-661*b* and through channels 630*a* and 630*b*, and engaging the vertebra disposed below the plate. The apertures 651*a*-651*b* can be substantially wide enough to enable a width of a fastener 640, including threads, to pass through. In an embodiment, the attachment cross-links 650 and 660 are not fixed in position relative to plate 610. Rather, attachment cross-links 650 and 660 can move atop the plate 610 as the fasteners glide through channels 630*a* and 630*b*. In some embodiments, all of the attachment cross-links 650 and 660 are fixed. In other embodiments, all of the attachment cross-links are dynamic relative to plate 610. Some embodiments of device 600 comprise both dynamic and fixed attachment cross-links 650 and 660.

Figure 6B:
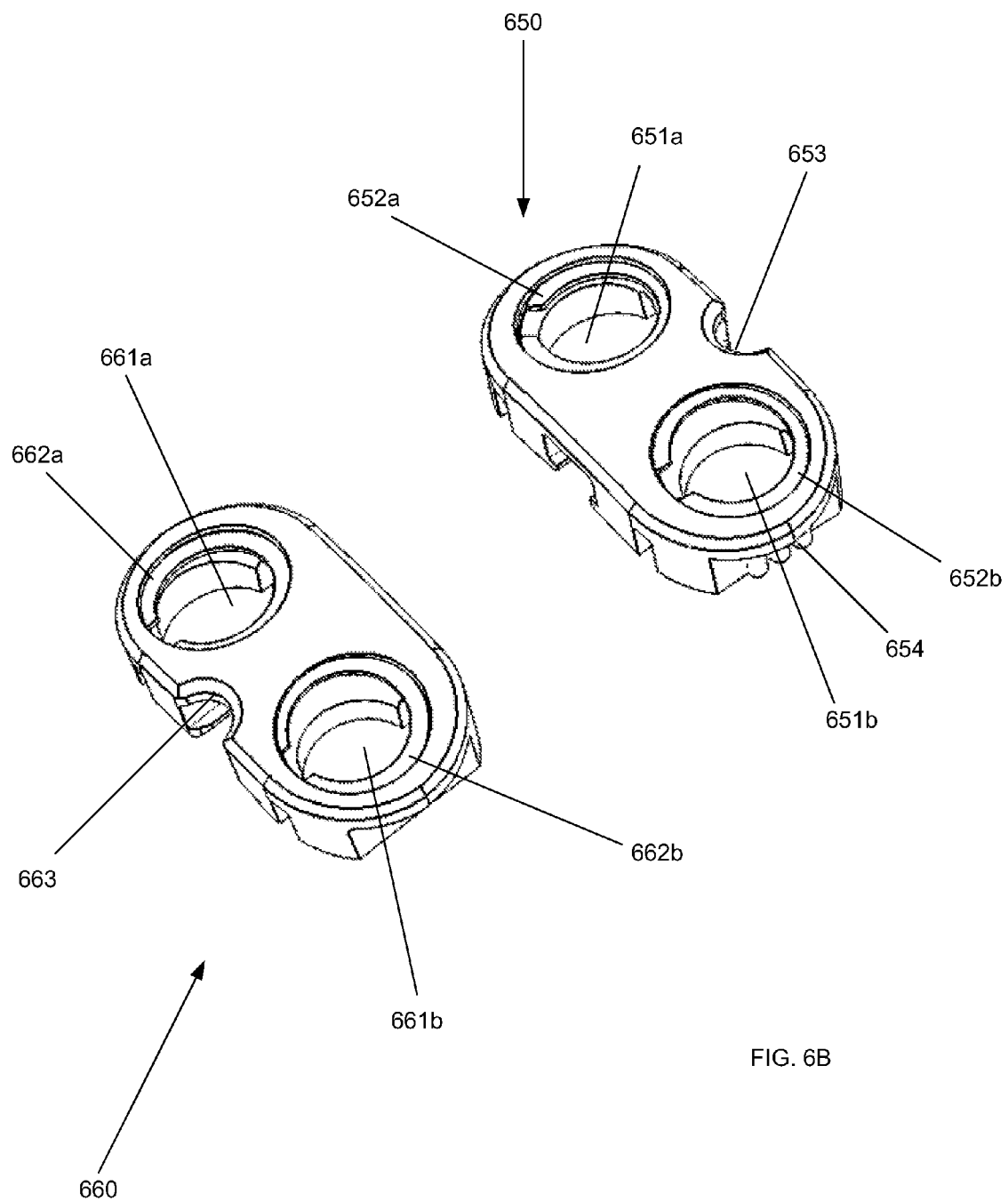
FIG. 6B illustrates an embodiment of attachment cross-links of an exemplary embodiment of the present invention.

FIG. 6B illustrates attachment cross-links 650 and 660 according to an embodiment of the present invention. As described above, an embodiment of the present invention can comprise an attachment cross-link 650-660 that can be configured to couple to the elongate plate 610 and to threading fasteners through apertures 651*a*-651*b* and 661*a*-661*b* and the channels, and engage the vertebra disposed below the plate 610. In some embodiments, the apertures can comprise a c-clip spacer 652*a-b* and 662*a-b* substantially within an interior volume of the aperture. The c-clip spacer 652*a-b* and 662*a-b* can be configured to serve as a spacer/seal between a surface of a crosslink and a surface of a fastener. In an embodiment, the apertures 651*a*-651*b* and 661*a*-661*b* can comprise female helical threads adapted to receive threading fasteners through the apertures.

In an embodiment of the present invention, the attachment cross-links 650 and 660 can further comprise an alignment guide, 653 and 663, configured to define a fastener placement angle. The alignment guide can comprise an indicator 653 and 663. In some embodiments, the indicator 653 and 663 can comprise a notch in an outer surface of the attachment cross-link. The alignment guide can comprise many different indicators known in the art including, but not limited to, a notch, an arrow, an indentation, a bump, a dot, and the like.

In an embodiment of the present invention, the attachment cross-link 650 can be dynamic and move along the elongate channel. In an embodiment where the attachment cross-link can be dynamic and move along the elongate channel, there may not be channel grooves on the interior surface of the elongate channels. Similarly, there may not be cross-link grooves on the outer surface of the attachment cross-links, thus allowing the attachment cross-link to move dynamically along the elongate channel.

Alternatively, the attachment cross-link 650 can be static, or fixed, with respect to the elongate channel. The cross-link 650 can be fixed by engaging the attachment cross-link grooves 654 with the channel grooves for fixation. In some embodiments, the elongate plate 610 can comprise both dynamic and static attachment cross-links. In an embodiment, the elongate plate can comprise two or more attachment cross-links 650 and 660 that can be dynamically coupled to the plate 610 with the end attachment cross-links being statically coupled to the plate, thus allowing the center vertebrae to be optimally fixed by adjusting the position of the dynamic attachment cross-links.

In an embodiment of the present invention, the pull out strength of the plate 610 can be strong enough that once the fasteners are engaged to the vertebrae, the cross-links and fasteners cannot easily be pulled away from the plate itself and the vertebral body.

Figure 6C:
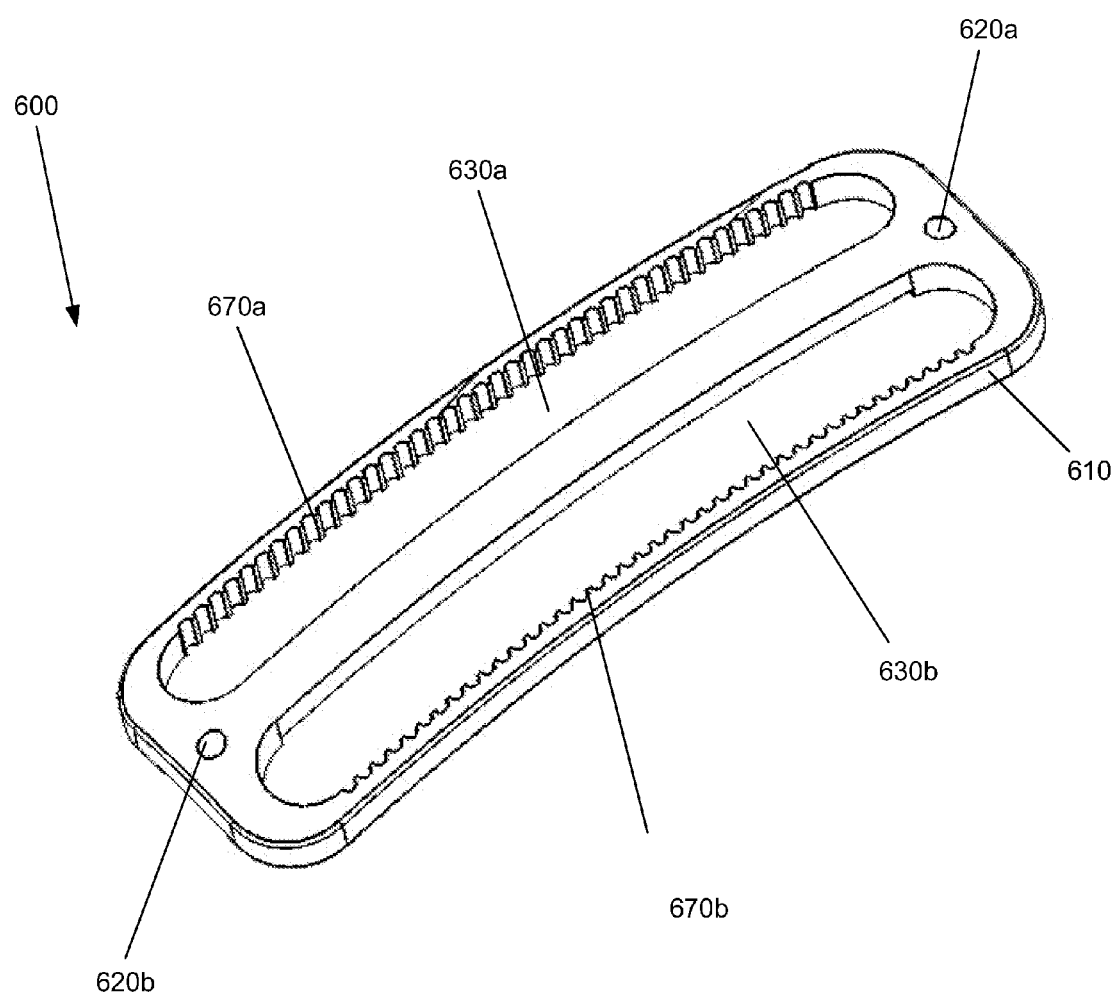
FIG. 6C illustrates a top view of a plate of an exemplary embodiment of the present invention.

FIG. 6C illustrates a plate 610 in an exemplary embodiment of the present invention. In an embodiment of the present invention, the elongate channels 630*a* and 630*b* can be substantially equal in length. The elongate channels 630*a*-630*b* can extend substantially from the distal end to the proximal end of the elongate plate 610. In some embodiments, the elongate channels 630*a* and 630*b* can continuously extend substantially from the distal end to the proximal end of the elongate plate 610. In an embodiment, the elongate channels 630*a*-630*b* can comprise channel grooves 670*a* and 670*b* disposed on at least one side of an interior surface of the channel 630*a* and 630*b* for engaging corresponding grooves on the cross-links. In an embodiment, the elongate plate 610 can have an anterior side and a posterior side. In an embodiment, the posterior elongate channel 630*b* can comprise channel grooves 670*b* disposed on the posterior side of the interior surface of the posterior elongate channel 630*b* and the anterior elongate channels 630*a* can comprise channel grooves 670*a* disposed on the anterior side of the interior surface of the anterior elongate channel 630*a*.

The elongate plate 610 can be various shapes suitable for extending between vertebrae, such as, but not limited to, rectangular, square, oval, trapezoidal, circular, and the like.

In an embodiment of the present invention, the plate 610 can have a thickness from about 0.5 mm to about 5 mm. In some embodiments, the plate 610 can have a thickness from about 1 mm to about 4 mm. In an embodiment, the plate 610 can have a thickness from about 1.5 mm to about 3 mm. In an embodiment, the plate 610 can have a thickness from about 1.8 mm to about 2.2 mm. In one embodiment, the plate 610 can have a thickness from about 2 mm to about 2.25 mm. In an embodiment, the plate 610 can have a thickness of about 2 mm. In another embodiment, the plate can have a thickness of about 2.25 mm.

In an embodiment of the present invention, the elongate channels 630*a* and 630*b* may have a length suitable for positioning cross-link members adjacent various vertebrae. In an embodiment of the present invention, the elongate channels 630*a* and 630*b* can have a length from about 3 mm to about 10 mm. In some embodiments, the elongate channels 630*a* and 630*b* can have a length from about 4 mm to about 8 mm. In an embodiment, the elongate channels 630*a* and 630*b* can have a length from about 5 mm to about 7 mm. In an embodiment, the elongate channels 630*a* and 630*b* can have a length from about 5.5 mm to about 6.5 mm. In an embodiment, the elongate channels 630*a* and 630*b* can have a length of about 6 mm.

The elongate plate 610 can further comprise a distal aperture 620*a* and a proximal aperture 620*b*. The apertures 620*a*-620*b* can be configured to fix the distal and proximal ends of the plate. The center vertebrae can be optimally fixed by adjusting the position of the attachment cross-links. In an embodiment of the present invention, the elongate channels 630*a* and 630*b* can extend substantially from the distal aperture to the proximal aperture.

Figure 6D:
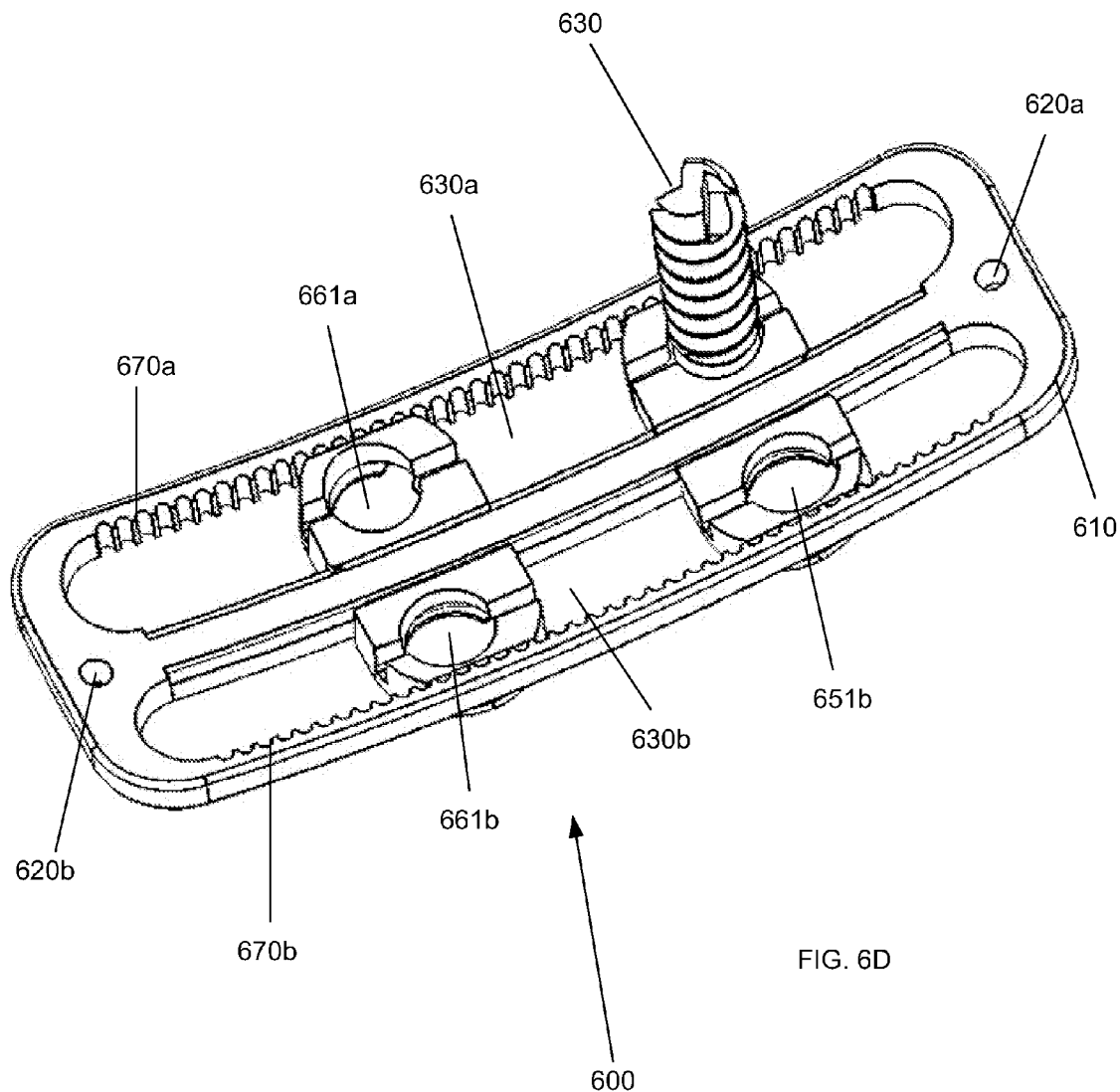
FIG. 6D illustrates a bottom view of a plate and attachment cross-links of an exemplary embodiment of the present invention.

FIG. 6D illustrates a bottom view of the vertebral stabilization device 600 of the present invention. In an embodiment of the present invention, the attachment cross-links 650 and 660 are flush with the top surface of the plate 610. In some embodiments, the elongate channels 630*a*-630*b* can further comprise a recessed portion disposed therein configured to be in communication with the attachment cross-links 650 and 660 such that the attachment cross-links 650 and 660 can be flush with the top surface of plate. In an embodiment, the attachment cross-links 650 and 660 are not flush with the top surface of the plate.

Figure 7A:
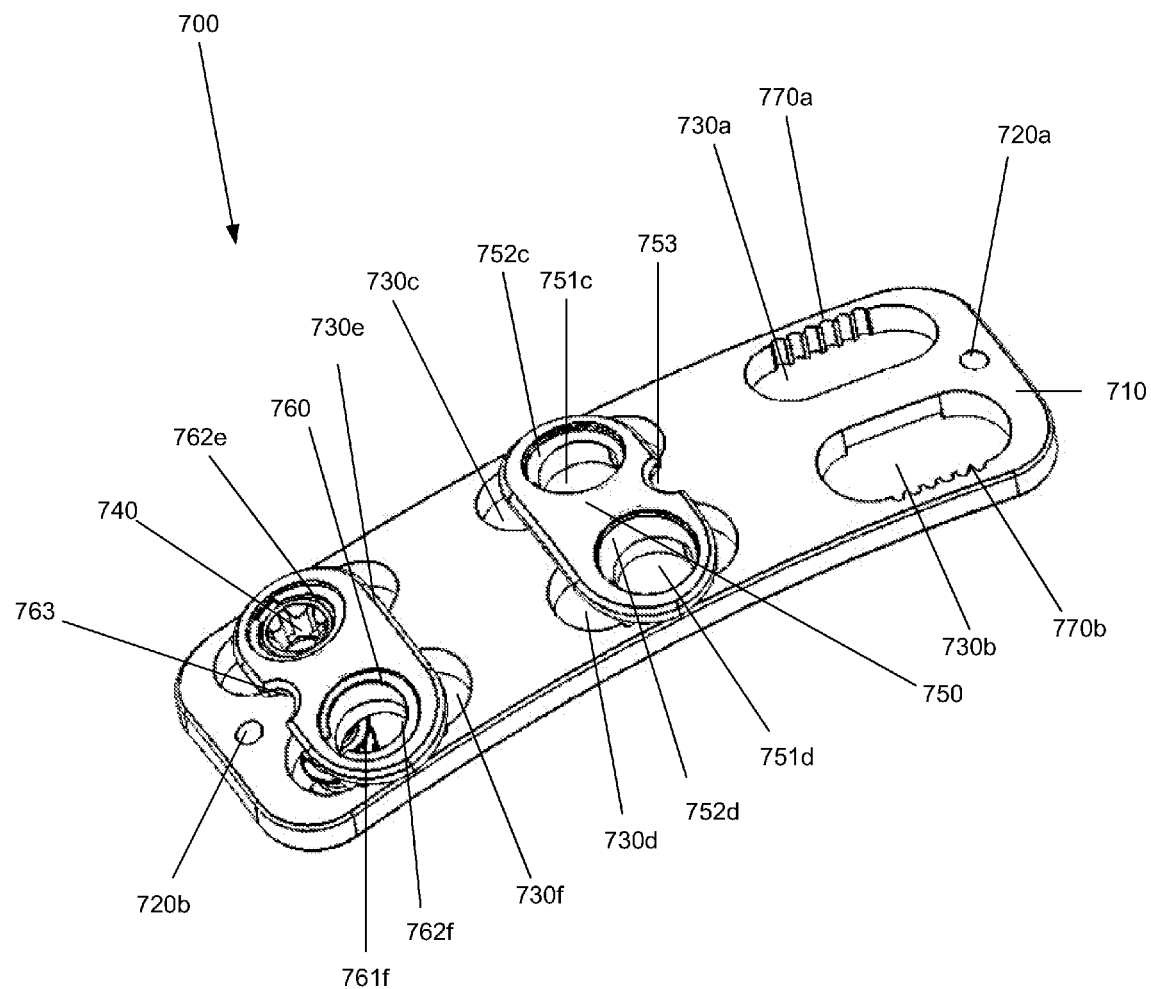
FIG. 7A illustrates a top view of a plate and attachment cross-links of an exemplary embodiment of the present invention.
Figure 7B:
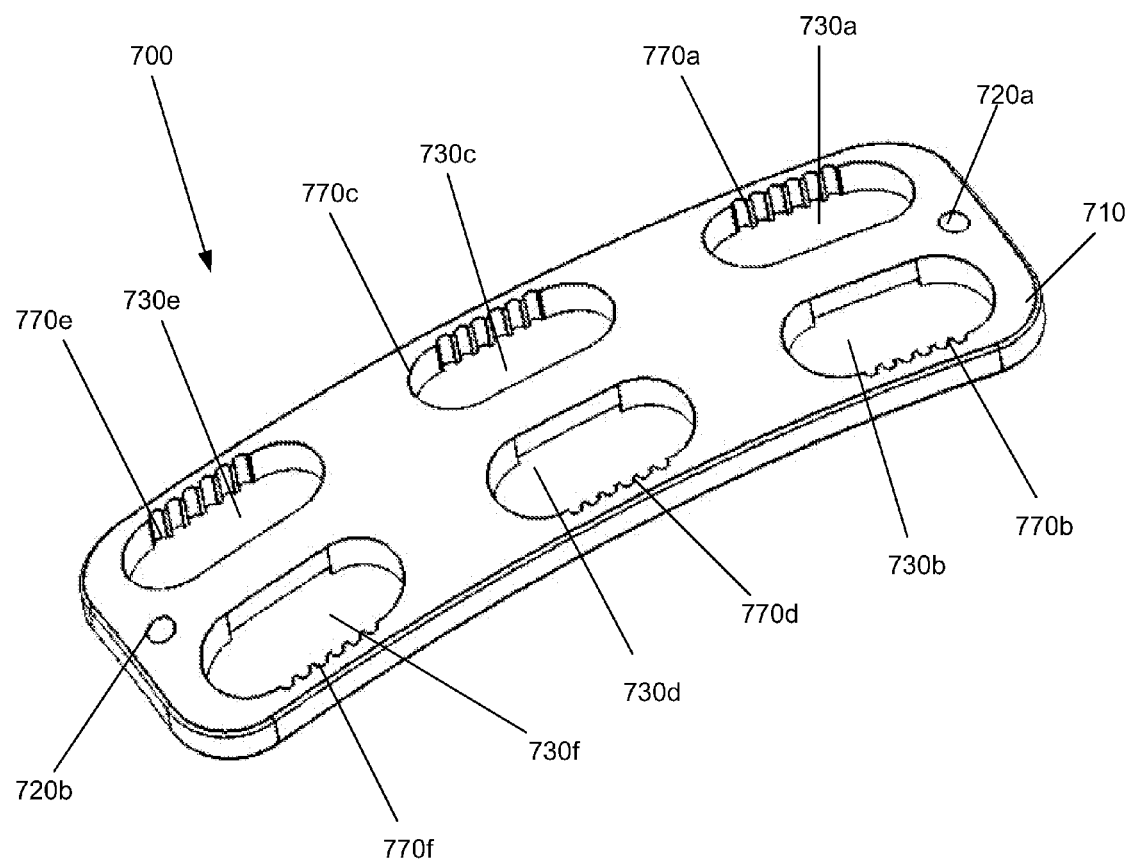
FIG. 7B illustrates a top view of a plate of an exemplary embodiment of the present invention.
Figure 7C:
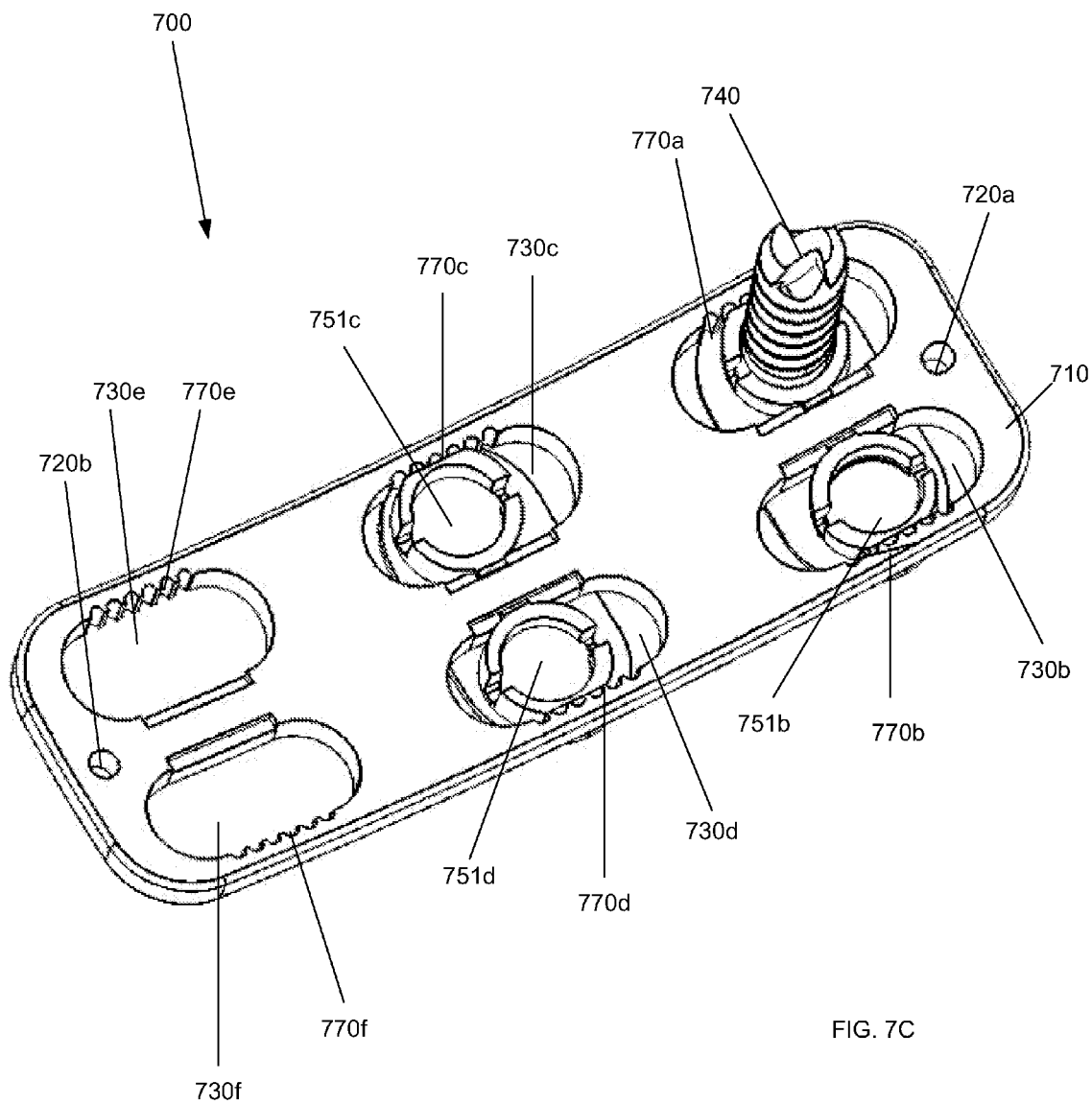
FIG. 7C illustrates bottom view of a plate and attachment cross-links of an exemplary embodiment of the present invention.

FIG. 7A illustrates a top view of a vertebral stabilization device 700 that can comprise plate 710 and a plurality of channels 730a-730f. The elongate plate 710 can have a distal end and a proximal end and can have an anterior side and a posterior side. In an embodiment, the plate 710 can comprise a first elongate channel 730a and a second elongate channel 730b. In an embodiment, the plate 710 can further comprise a third elongate channel 730c and a fourth elongate channel 730d. The channels 730a-730b can extend along at least a portion of the plate between the distal end and the proximal end. In an embodiment, the first 730a and second 730b elongate channels can be substantially parallel. The third 730c and fourth 730d elongate channels can also be substantially parallel.

Other contemplated embodiments can comprise a fifth elongate channel 730e and a sixth elongate channel 730f, or more, with corresponding attachment cross-links, 750 and 760, for example, according to the number of channels disposed within the plate. In some embodiments, there can be one attachment cross-link corresponding to every two elongate channels. In some embodiments, there can be a plurality of attachment cross-links corresponding to every two elongate channels.

Figure 8:
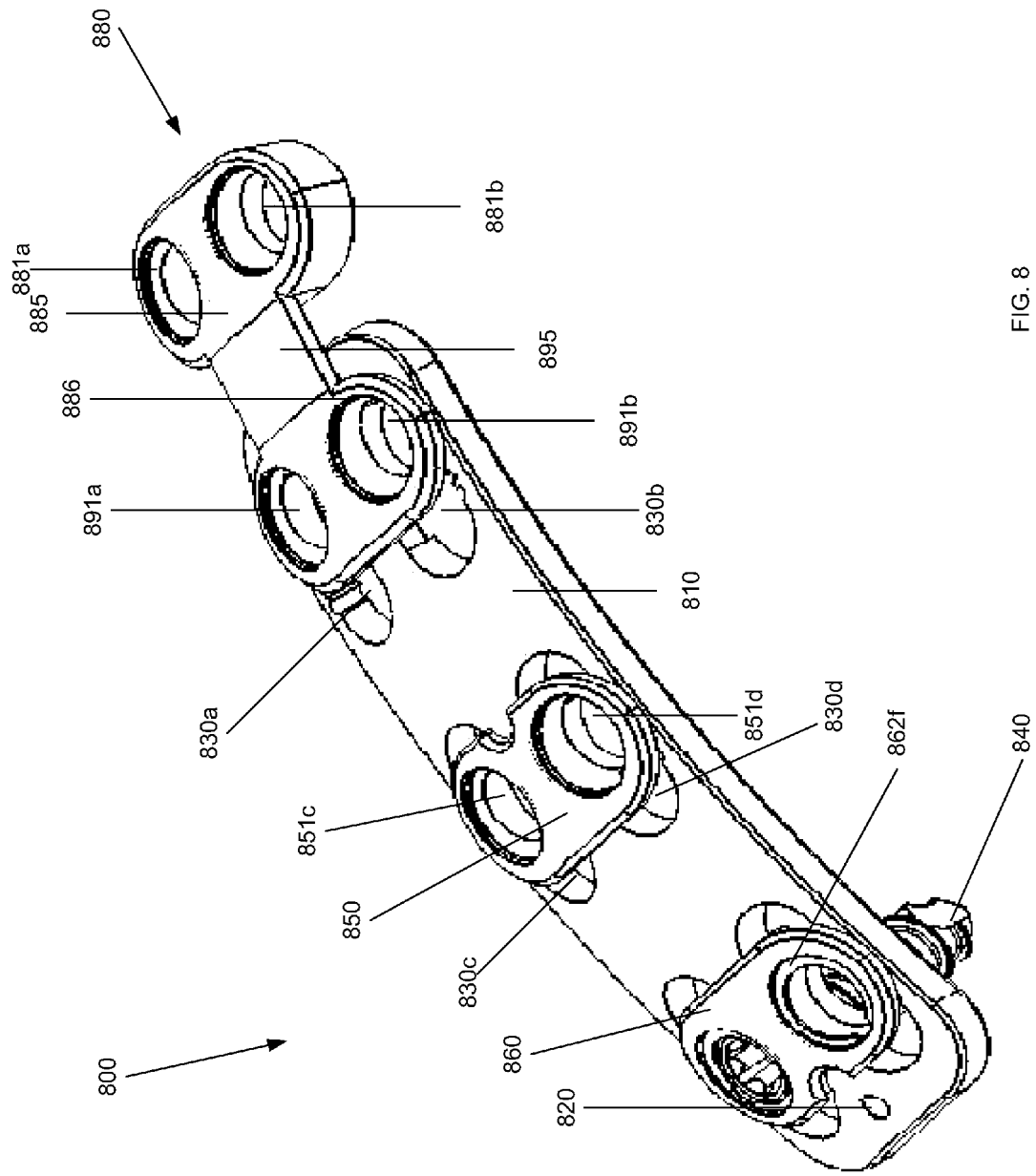
FIG. 8 illustrates a top view of a plate, attachment cross-links and an extension adapter of an exemplary embodiment of the present invention.

FIG. 8 illustrates a top view of a vertebral stabilization device 800 comprising extension adapter 880. An embodiment of the present invention can comprise an extension adapter 880 configured to allow adjacent level incorporation without removal of the plate 810 during a revision. At the time of revision, the distal or proximal attachment cross-link can be removed and the extension adapter cross-links 885 and 886 can be engaged with the plate 810. In an embodiment, the extension adapter 880 can comprise a plurality of extension adapter cross-links 885 and 886. The extension adapter 880 can be configured to couple to the plate 810 via the extension adapter cross-links 885 and 886 and by threading fasteners through apertures 881a-881b and 891a-891b and channels 830a-830b, and engage the vertebra disposed below the plate 810. The plurality of extension adapter cross-links 885 and 886 can be configured similarly to other attachment cross-links described above. In an embodiment of the present invention, the extension adapter cross-links can be static. In embodiments where the extension adapter cross-links are static, the adapter cross-links can comprise grooves that can be configured to cooperatively engage the channel grooves of the elongate channels.

In an embodiment, the adapter cross-links can be dynamic and move along the elongate channels. In embodiments where the extension adapter cross-links are dynamic, the adapter cross-links may not comprise adapter grooves. Additionally, the elongate channels may not comprise channel grooves in embodiments where the adapter cross-links are dynamic.

In some embodiments, the apertures 881a-881b and 891a-891b can comprise a c-clip spacer substantially within an interior volume of the aperture. In an embodiment, the apertures 881a-881b and 891a-891b can comprise female helical threads adapted to receive threading fasteners through the apertures.

In an embodiment, the extension adapter 880 can have the same thickness as the plate 810 and therefore can have substantially the same profile as the plate 810. The extension adapter 880 can comprise a bridge 895 that connects the adapter 880 to the plate 810. In an embodiment, the bridge 895 can have a thickness less than the thickness of the extension adapter cross-links 885 and 886 such that the overall plate height can be equal between the main plate 810 and the extension adapter 880. In some embodiments, the bridge 895 can have a thickness from about 0.5 mm to about 1.2 mm. In some embodiments, the bridge 895 can have a thickness from about 0.7 mm to about 1.0 mm. In an embodiment, the bridge 895 can have a thickness of about 0.8 mm.

It should be apparent to those skilled in the art to which this disclosure pertains that there are several advantages to the devices and methods disclosed herein. In general, the device provides one system for both simple and complex cases. Additionally, a surgeon can change from a static to a dynamic plate easily depending on the situation. Furthermore, the device can also be a hybrid type plate, that is, with both static and dynamic capabilities. The dynamic movement of the attachment cross-links to fix the center vertebrae can allow the surgeon to have maximal flexibility in placing the intervening cross links while the end cross links can be static or dynamic. A further advantage of the plate is that it can be easily assembled once the surgeon has estimated the length needed. Additionally, the device of the present invention can be inexpensive to manufacture, simple to use and require minimal inventory for doctor's offices and/or hospitals. It can also be adjustable for complex reconstructions and allow for intra-operative flexibility.

The various embodiments described above are intended to enable a surgeon to intraoperatively customize the anterior cervical instrumentation system for optimal application. Consequently, the embodiments described above are merely exemplary and not limiting. In particular, the configurations, dimensions and orientation of components described above may be modified from what has been recited and described without departing from the design of the invention. Further, embodiments of the present invention are not limited to applications in the anterior region of the spine. Particularly, the embodiments of the present invention can also be used in the thoracic and lumbar regions.

What is claimed is:

1. A vertebral stabilization device, comprising:
   a vertebral stabilizing plate having an elongate channel, the elongate channel having an interior surface with a plurality of channel grooves;
   a first bridge, having a distal end and a proximal end;
   a first attachment cross-link attached to the proximal end of the bridge, the attachment cross-link having an aperture adapted to be fastened to the elongate channel of the vertebral stabilizing plate, and an attachment groove disposed on at least a portion of an outer surface of the first attachment cross-link adapted to cooperatively engage one or more of the plurality of channel grooves of the vertebral stabilizing plate; and
   a first extension cross-link, attached to the distal end of the bridge, the extension cross-link having an aperture.

2. The device of claim 1, wherein the interior of the aperture of the first attachment cross-link is frusto-conically shaped.

3. The device of claim 1, wherein the interior of the aperture of the first attachment cross-link comprises female helical threads.

4. The device of claim 1, wherein the interior of the aperture of the first attachment cross-link comprises a c-clip spacer.

5. The device of claim 1, wherein the first attachment cross-link is adapted to be slidably fastened to the elongate channel of the vertebral stabilizing plate.

6. The device of claim 1, wherein the first attachment cross-link is approximately 14-18 mm wide.

7. The device of claim 1, wherein the first attachment cross-link is approximately 1-3 mm thick.

8. The device of claim 1, the vertebral stabilization device further comprising:
   a second bridge having a distal end and a proximal end, wherein the first extension cross-link is attached to the proximal end of the second bridge; and
   a second extension cross-link attached to the distal end of the second bridge, the second extension cross-link having an aperture.

9. The device of claim 1, the vertebral stabilization device further comprising:
   a second bridge having a distal and a proximal end;
   a second attachment cross-link attached to the proximal end of the second bridge, having an aperture adapted to be fastened to the first extension cross-link; and
   a second extension cross-link attached to the distal end of the second bridge, having an aperture.

10. The device of claim 1, wherein the first attachment cross-link further comprises an alignment guide.

11. The device of claim 10, wherein the alignment guide comprises a notch, arrow, indentation, bump or dot in an outer surface of the first attachment cross-link.

12. The device of claim 1, wherein the first extension cross-link is approximately the same thickness as the vertebral stabilizing plate.

13. The device of claim 12, wherein an outer surface of the first attachment cross-link, when placed on the vertebral stabilizing plate, is approximately flush with an outer surface of the vertebral stabilizing plate.

\* \* \* \* \*